(12) United States Patent
Boudreaux et al.

(10) Patent No.: US 10,105,144 B2
(45) Date of Patent: Oct. 23, 2018

(54) SURGICAL CLIP AND APPLIER DEVICE AND METHOD OF USE

(71) Applicant: Ethicon Endo-Surgery, Inc., Cincinnati, OH (US)

(72) Inventors: Chad P. Boudreaux, Cincinnati, OH (US); Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 79 days.

(21) Appl. No.: 14/547,725

(22) Filed: Nov. 19, 2014

(65) Prior Publication Data
US 2015/0080915 A1    Mar. 19, 2015

Related U.S. Application Data

(60) Continuation of application No. 13/026,675, filed on Feb. 14, 2011, now Pat. No. 8,915,931, which is a
(Continued)

(51) Int. Cl.
*A61B 17/10* (2006.01)
*A61B 17/128* (2006.01)
(Continued)

(52) U.S. Cl.
CPC ........ *A61B 17/1285* (2013.01); *A61B 17/064* (2013.01); *A61B 17/1227* (2013.01);
(Continued)

(58) Field of Classification Search
CPC .......... A61B 17/064; A61B 2017/0645; A61B 17/07207; A61B 17/1227; A61B 17/1285
See application file for complete search history.

(56) References Cited

U.S. PATENT DOCUMENTS

| 3,446,212 A | 5/1969 | Le Roy |
| 3,458,110 A | 7/1969 | Goldman |

(Continued)

FOREIGN PATENT DOCUMENTS

| JP | 5038693 U | 4/1975 |
| JP | 06001094 A | 1/1994 |

(Continued)

OTHER PUBLICATIONS

Extended European Search Report issued in European Application No. 06255982.8 dated Jun. 19, 2007.
(Continued)

*Primary Examiner* — Kathleen Holwerda
*Assistant Examiner* — Sarah Simpson
(74) *Attorney, Agent, or Firm* — Mintz Levin Cohn Ferris Glovsky and Popeo, P.C.

(57) ABSTRACT

A surgical clip is provided for ligating or transecting tissue, such as vessels, other tubular ducts, and the like and a surgical clip applier device for delivering and applying the surgical clip to the tissue. The surgical clip can include a spine and opposed arms extending from the spine where the arms can define a clamping length. In a resting state, the clip can be biased to a closed position such that the ends of each opposed arm are disposed in proximity to each other. With such biasing, when applied to a tissue, such as with a surgical clip applier, the clip can exert a positive clamping pressure to the tissue along the clamping length to seal the tissue and limit passage of fluids, such as blood, from the tissue.

17 Claims, 26 Drawing Sheets

Related U.S. Application Data division of application No. 11/286,889, filed on Nov. 23, 2005, now Pat. No. 7,896,895.

(51) Int. Cl.
  *A61B 17/064* (2006.01)
  *A61B 17/122* (2006.01)
  *A61B 17/072* (2006.01)
  *A61B 17/00* (2006.01)
  *A61B 90/00* (2016.01)

(52) U.S. Cl.
  CPC ... *A61B 17/072* (2013.01); *A61B 2017/00862* (2013.01); *A61B 2017/07221* (2013.01); *A61B 2090/037* (2016.02)

(56) References Cited

U.S. PATENT DOCUMENTS

| | | | |
|---|---|---|---|
| 3,604,425 A | 9/1971 | Le Roy | |
| 4,671,278 A | 6/1987 | Chin | |
| 4,791,707 A | 12/1988 | Tucker | |
| 4,796,627 A | 1/1989 | Tucker | |
| 5,207,692 A | 5/1993 | Kraus et al. | |
| 5,219,354 A * | 6/1993 | Choudhury | A61B 17/0644 606/142 |
| 5,342,373 A | 8/1994 | Stefanchik et al. | |
| 5,368,600 A | 11/1994 | Failla et al. | |
| 5,389,098 A * | 2/1995 | Tsuruta | A61B 17/00234 606/142 |
| 5,439,468 A | 8/1995 | Schulze et al. | |
| 5,447,513 A | 9/1995 | Davison et al. | |
| 5,501,693 A | 3/1996 | Gravener | |
| 5,624,452 A | 4/1997 | Yates | |
| 5,626,585 A | 5/1997 | Mittelstadt et al. | |
| 5,645,567 A | 7/1997 | Crainich | |
| 5,681,330 A | 10/1997 | Hughett et al. | |
| 5,779,720 A | 7/1998 | Walder-Utz et al. | |
| 5,858,018 A | 1/1999 | Shipp et al. | |
| 6,001,110 A | 12/1999 | Adams | |
| 6,165,204 A * | 12/2000 | Levinson | A61B 17/0487 606/151 |
| 6,277,131 B1 | 8/2001 | Kalikow | |
| 6,572,626 B1 | 6/2003 | Knodel et al. | |
| 6,607,540 B1 | 8/2003 | Shipp | |
| 6,607,542 B1 * | 8/2003 | Wild | A61B 17/122 606/139 |
| 6,942,675 B1 * | 9/2005 | Vargas | A61B 17/07207 227/175.1 |
| 7,052,504 B2 | 5/2006 | Hughett | |
| 7,179,265 B2 | 2/2007 | Manetakis et al. | |
| 7,896,895 B2 | 3/2011 | Boudreaux et al. | |
| 8,915,931 B2 | 12/2014 | Boudreaux et al. | |
| 2002/0177859 A1 | 11/2002 | Monassevitch et al. | |
| 2003/0014060 A1 | 1/2003 | Wilson et al. | |
| 2004/0193185 A1 | 9/2004 | McBrayer | |
| 2005/0070925 A1 * | 3/2005 | Shelton, IV | A61B 17/07207 606/142 |
| 2005/0165422 A1 | 7/2005 | Wilson | |
| 2005/0288689 A1 | 12/2005 | Kammerer et al. | |
| 2007/0118163 A1 | 5/2007 | Boudreaux et al. | |
| 2011/0137324 A1 | 6/2011 | Boudreaux et al. | |

FOREIGN PATENT DOCUMENTS

| | | |
|---|---|---|
| JP | 2000255661 A | 9/2000 |
| JP | 2003313133 A | 11/2003 |
| JP | 3099945 U | 4/2004 |
| JP | 3102614 U | 7/2004 |
| WO | 0135832 A2 | 5/2001 |

OTHER PUBLICATIONS

Office action issued in Australian Application No. 2006236074 dated Apr. 10, 2012.
Office action issued in Australian Application No. 2006236074 dated Dec. 9, 2011.
Office action issued in Chinese Application No. 200610146845.7 dated Aug. 21, 2009.
Office action issued in Chinese Application No. 20061014685.7, dated Aug. 21, 2008.
Office action issued in European Application No. 06255982.8 dated Feb. 26, 2008.
Office action issued in Japanese Application No. 2006-315809 dated Dec. 13, 2011.
Partial European Search Report issued in European Application No. 06255982.8 dated Mar. 29, 2007.

* cited by examiner

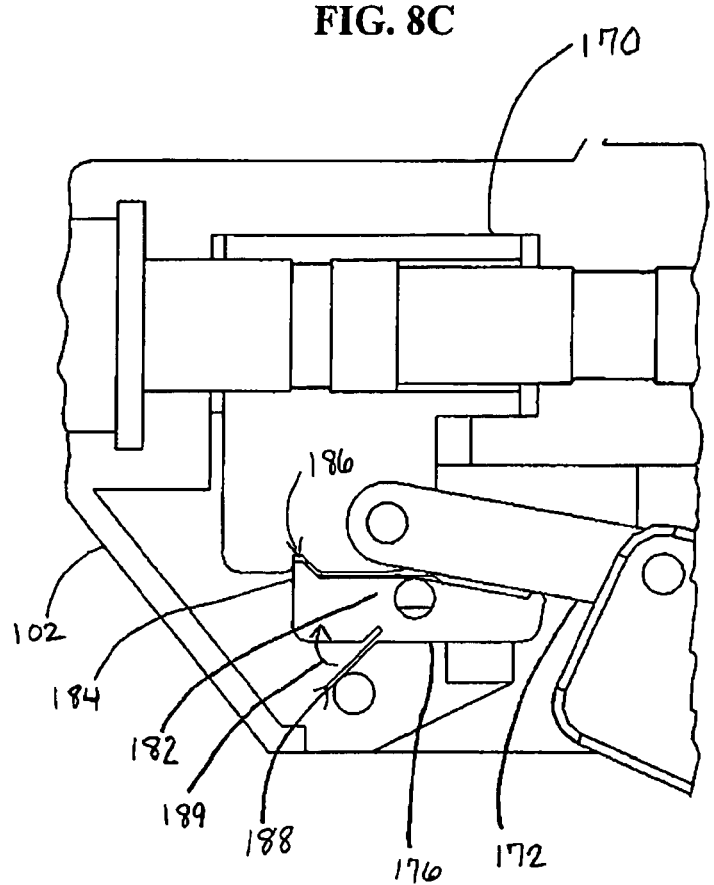

SURGICAL CLIP AND APPLIER DEVICE AND METHOD OF USE

CROSS REFERENCE TO RELATED APPLICATIONS

This application is a continuation of U.S. application Ser. No. 13/026,675 filed Feb. 14, 2011 and entitled "Surgical Clip and Applier Device and Method of Use," which is a divisional of U.S. application Ser. No. 11/286,889 filed on Nov. 23, 2005 and entitled "Surgical Clip Applier Device and Method of Use," which is hereby incorporated by reference in its entirety.

FIELD OF THE INVENTION

The invention relates broadly to surgical devices, and more particularly to surgical clips, surgical clip appliers, and methods used for ligating vessels, other ducts, and the like.

BACKGROUND OF THE INVENTION

In recent years, surgery has markedly advanced through the performance of laparoscopic and endoscopic surgical procedures. Endoscopic procedures are performed through natural orifices, whereas laparoscopic surgical procedures are often accomplished through an access port such as a trocar assembly, which is a surgical instrument used to puncture a body cavity. The trocar typically contains a sharpened obturator tip and a trocar tube or cannula. The trocar cannula is inserted into the skin to access the body cavity, by using the obturator tip to penetrate the skin. After penetration, the obturator is removed and the trocar cannula remains in the body.

During many surgical procedures, a surgeon will have to close or ligate various blood vessels, ducts, and other tissues before severing them in order to prevent excessive bleeding, and to reduce the risk of other complications to the patient. It is also sometimes necessary to transect a vessel, duct, or organ by cutting and then sealing both ends of the vessel, duct, or organ using an instrument such as a linear cutter/stapler.

One surgical instrument that is commonly used endoscopically or laparoscopically ligate a vessel, duct, or organ is a surgical clip applier for ligating a blood vessel, a duct, shunt, or a portion of body tissue during surgery. Clip appliers typically have a handle with an elongate shaft having a pair of movable opposed jaws formed on an end thereof for holding and forming a ligation clip therebetween. The jaws are positioned around the vessel and the clip is secured to the vessel via mechanical deformation caused by closing of the jaws.

One drawback associated with some current clips used for ligating vessels is that the legs of the clip tend to separate to some extent following release from a clip applier. This phenomenon is called duck-billing. Duck-billing can result in insufficient ligation of a vessel, thus leading to excessive blood loss and/or unnecessary damage to the vessel. Further, some ligation clips are often difficult to advance into the jaws of a clip applier because of resistance between the tissue disposed between the jaws and the gripping features on the clip legs.

Despite existing technologies, there remains a need for improved surgical clip appliers, clips, and methods used for ligating and transecting tissue, such as blood vessels, other ducts, and the like.

SUMMARY OF THE INVENTION

Embodiments of the present invention generally provide surgical clips, clip applying devices, and methods of ligating and transecting tissue.

In one aspect, a surgical clip is provided that comprises a spine having a height defined by a top edge and a bottom edge and extending along a longitudinal axis of the clip from a first clip end to a second clip end. The clip also has opposed arms that extend from the top and bottom edges of the spine, and the arms can be biased to a closed position such that ends of each opposed arm are disposed in proximity to each other to define a tissue-clamping region having a length. The clamping length is defined by the arms. The opposed arms of the surgical clip can have one or more slots disposed along the length of the clip, such that each slot extends from the ends of each opposed arm towards the spine in a direction substantially transverse to the longitudinal axis of the clip. In one embodiment, the surgical clip is frangible at one or more locations along the length such that the length of the tissue-clamping region can be selectively controlled. Further, the spine of the clip can be bendable along the longitudinal such that the shape of the clip can be selectively altered.

In another aspect, a surgical fastener delivery system includes a delivery device having a clip supply and a clip opening mechanism. The delivery device has a handle and an elongate shaft extending from the handle. The elongate shaft has opposed jaws disposed at a distal end of the elongate shaft and operable to move between an open, spaced-apart position and a closed position. The system further includes a surgical clip supply adapted to be disposed within the delivery device. The surgical clip supply includes at least one surgical clip having a spine and opposed arms extending therefrom, and the arms can be biased to a closed position such that ends of each arm are disposed in proximity to each other to define a clamping region. The clip opening mechanism is disposed within the delivery device and is operable to configure a surgical clip from the closed position to the open position such that ends of each arm are disposed in a spaced-apart position defining a tissue-receiving space. In one embodiment the delivery device can also include a cutting element disposed therein that is selectively moveable from a retracted position to an extended position relative to a distal end of the elongate shaft and operable to incise tissue disposed between the opposed jaws.

In a further aspect, a method for applying a surgical clip, comprises providing a surgical clip having opposed arms biased to a closed position such that ends of each opposed arm are disposed in proximity to each other; overcoming a biasing force of the surgical clip to separate the opposed arms to an open position; applying the surgical clip to tissue to be ligated; and allowing the clip to close to ligate or transected the tissue.

BRIEF DESCRIPTION OF THE DRAWINGS

The invention will be more fully understood from the following detailed description taken in conjunction with the accompanying drawings, in which:

FIG. 8C is a side view of a locking mechanism of the jaw closure assembly of FIG. 8B in an engaged state;

DETAILED DESCRIPTION OF THE INVENTION

Figure 1A:
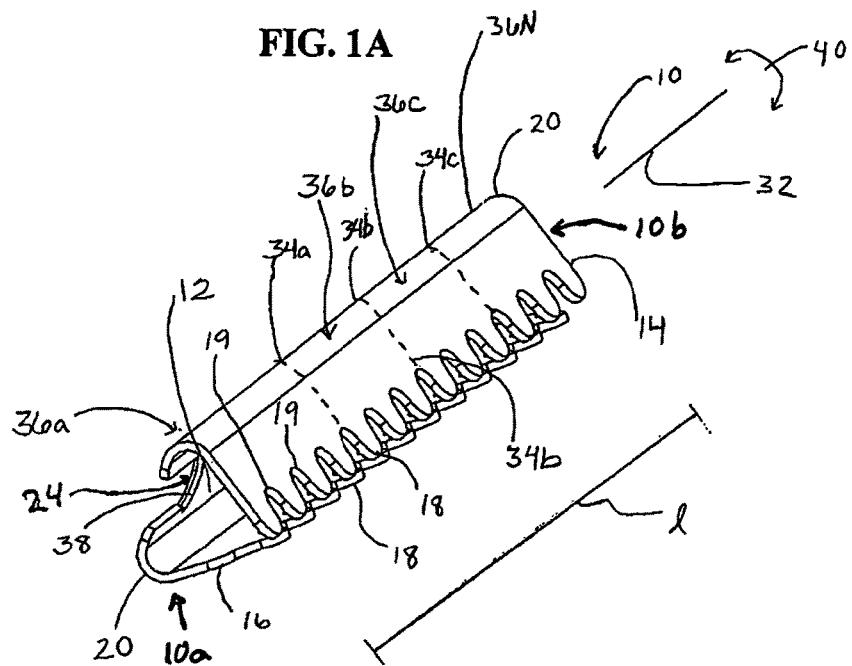
FIG. 1A is a perspective view of one embodiment of a surgical clip.

Certain exemplary embodiments will now be described to provide an overall understanding of the principles, structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

The present invention generally relates to surgical clips for ligating and transecting tissue, such as vessels, other tubular ducts, and the like, surgical clip appliers for delivering and applying surgical clips to tissue and methods for ligating tissue. While the devices and methods are described herein in the context of a device to ligate or transect vessels, one skilled in the art will appreciate that the devices and methods can be used to ligate or transect a variety of other body tissues, including but not limited to, veins, arteries, ducts, or any other tubular member within a patient for which ligation is desired.

FIGS. 1A-3 illustrate various exemplary embodiments of surgical clips. In one embodiment, shown in FIGS. 1A-1B, the clip 10 is a generally elongate body having a longitudinal axis 32, a spine 12 extending between first and second clip ends 10a, 10b. The spine 12 has a height h defined by a top edge 12a and a bottom edge 12b, as shown in FIG. 1B, and the opposed arms 14, 16 extend from the top and bottom edges of the spine 12 such that the arms are configured to clamp tissue therebetween. The length of the arms 14, 16, from the first 10a to the second 10b clip ends define a clamping length l.

Figure 1B:
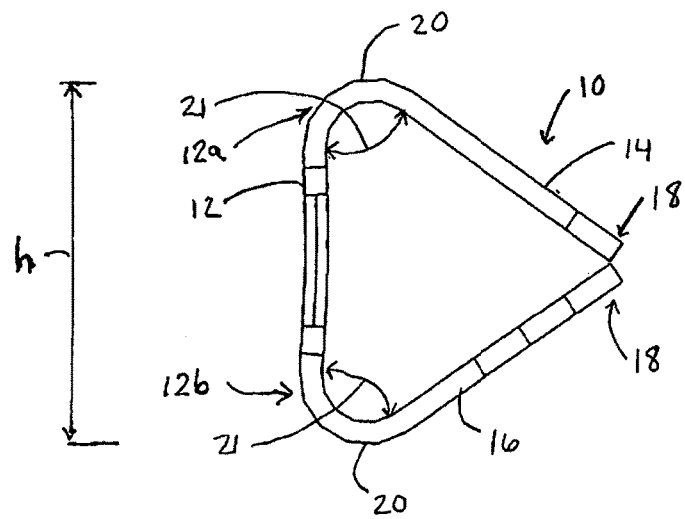
FIG. 1B is an end view of the surgical clip of FIG. 1A.

One skilled in the art will appreciate that the clip 10 can have physical properties that are appropriate for a desired application. In one exemplary embodiment as illustrated in FIGS. 1A and 1B, in a resting state, the clip 10 is biased to a closed position such that the ends of each opposed arm 14, 16 are disposed in proximity to each other to define a clamping region therebetween. In such a closed position, the arms 14, 16 may either be in contact with each other or in a spaced apart relationship. In either event, the biasing is such that, when applied to a tissue, the clip 10 can exert a positive clamping pressure to the tissue present in the clamping region along the clamping length l to seal the tissue and limit passage of fluids, such as blood, from the tissue. For example, when the clip 10 is to be applied to a tissue, the clip is placed in an open, delivery position in which the arms 14, 16 are distracted relative to each other such that the spine 12 and arms 14, 16 of the clip 10 form a generally U-shaped (FIG. 9C) or C-shaped (FIG. 3) channel 17. The arms 14, 16 are maintained in the distracted state as the clip 10 is advanced over a tissue portion such that the tissue becomes disposed within the channel 17. When released, the arms 14, 16 return to the biased closed position such that the arms 14, 16 clamp and seal the tissue disposed therebetween.

Figure 3:
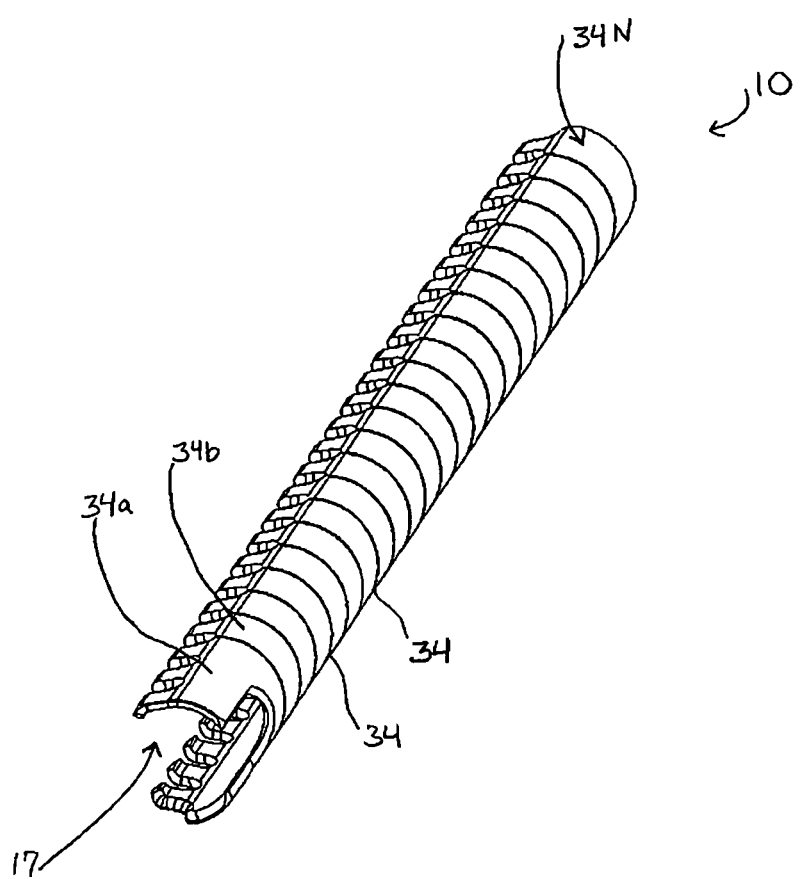
FIG. 3 is a perspective view of another embodiment of a surgical clip formed from a plurality of separable clip elements.

As indicated above, the clip 10 has a clamping length l that exerts a pressure on a tissue when the clip 10 is applied to the tissue. One skilled in the art will appreciate that the clamping length can vary in length relative to the length of the spine. That is, the clamping length can be greater than, less than, or equal to the length of the spine. In one embodiment, the clamping length l of the clip 10 can be selectively altered to correspond with a length of tissue to be ligated. For example, the clip 10 can be frangible at one or more locations 34 along a longitudinal axis of the clip 10 to allow the clamping length l of the clip 10 to be shortened. In particular, the material forming the clip 10 can be perforated, as indicated in FIG. 1A, or scored, as indicated in FIG. 3, at the locations 34 to allow the clip 10 to be separated into one or more clip elements 36a through 36n. In use, once a desired length of the clip 10 is applied to a tissue, such as clip portions 36a and 36b for example, a pressure or bending load can be applied to the clip 10 about location 34b to fracture the clip 10 at the location 34b and allow the unused clip elements 36c through 36n to be removed.

Figure 2:
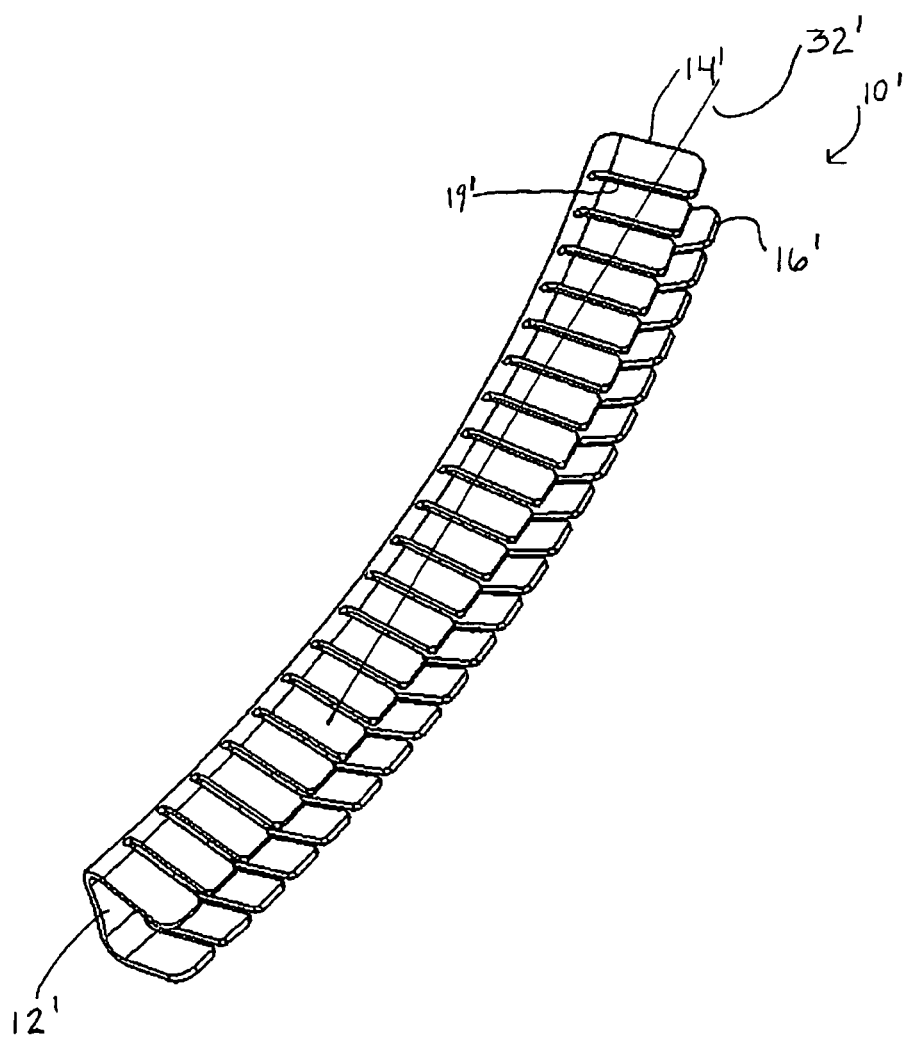
FIG. 2 is a perspective view of another embodiment of a surgical clip having a plurality of slots that separate adjacent arm segments of the clip.

The clip 10 can also have a selectively alterable shape such that the clip can be configured to conform to tissues having varying geometries. For example, the clip 10 can be bendable relative to a clip longitudinal axis 32. In one embodiment, the physical configuration of the clip 10 can affect the conformability of the clip. In particular, as shown in FIG. 1A, the clip 10 can include slots 19 that enable bending of the clip 10 to achieve a degree of conformability. As shown in FIG. 1A, slots 19 are relatively short and extend in a direction substantially transverse to longitudinal axis 32 from a position at or close to an end of the arms and they terminate well before spine 12. In another embodiment of the clip 10', as shown in FIG. 2, slots 19' extend over a greater distance between the end of each opposed arm 14', 16' and a location in relatively close proximity to the spine 12'. Such a configuration can provide a relatively large degree of conformability to the clip 10' to allow the clip 10' to be flexed relative to the longitudinal axis 32'.

The clip 10 can be formed from a variety of materials that bias the device to a closed position, but in an exemplary embodiment, it is formed from a spring material. For example, the clip 10 can be formed from a spring material such as a metal, metal alloy, or polymer. By way of non-limiting example, suitable metals can include spring steel, stainless steel, and alloys thereof. The clip can also be formed from a superelastic metal, such as an alloy of titanium and nickel (e.g., nitinol), that changes its shape upon the application of a force, such as a tension, and that returns to its deployed state upon removal of the force. Additionally, the clip 10 can be formed of a bioabsorbable polymer such as, by way of non-limiting example, polyglycolide, polydioxanone, or polylactide.

While the clip 10 can be biased to a closed, tissue-clamping position, one skilled in the art will understand that the geometric configuration of the clip 10 can also affect the bias of the opposed arms 14, 16. For example, the clip 10 can include bend portions 20 disposed between the opposed arms 14, 16 and the spine 12, where the bend portions 20 cause each of the opposed arms 14, 16 to form acute angles 21 relative to the spine 12. As such, the bend portions 20 orient the ends of arms 14, 16 toward each other when the clip 10 is in the biased closed position.

The opposed arms 14, 16 can include features that provide a more secure ligation of the vessel or duct. For example, the opposed arms 14, 16 can include one or more tissue-grasping elements 18 extending from the ends of the arms 14, 16 and disposed along the clamping length l. In use, when the clip 10 is placed on a portion of tissue, the tissue grasping elements 18 engage the tissue portion to secure the clip 10 to the tissue and minimize inadvertent movement of the clip 10 relative to the tissue. One skilled in the art will understand that the tissue grasping elements 18 can be disposed along the length l of the clip 10 in a variety of ways. In one embodiment, the tissue grasping elements 18 of the first arm 14 can be staggered relative to the tissue grasping elements 18 of the opposed second arm 16 along the clamping length l. For example, each of the arms 14, 16 includes slots 19 disposed between and separating adjacent tissue grasping elements 18 where each tissue grasping element 18 of the first arm 14 aligns with an opposed slot 19 of the second arm 16 and each tissue grasping element 18 of the second arm 16 aligns with an opposed slot 19 of the first arm 16. Alternatively, the arms 14, 16 of the clip 10 can be configured in a non-staggered manner such that the opposed tissue grasping elements of each arm are located opposite to each other.

The clip 10 can be used in conjunction with a clip applier, an example of which will be described in detail below, and the clip applier can optionally have a cutting element effective to incise a portion of tissue prior to application of the clip 10 thereto.

While the clip 10 can be used with a delivery device that includes a cutting element to provide incision of a tissue, one skilled in the art will understand that an incising element can be integrally formed on one end of the clip 10 to allow the clip 10 to incise tissue when applied thereto. In particular, as shown in FIG. 1A, a portion of the leading edge 24 of the spine 12 can be sharpened to form a cutting blade 38. In use, after the arms 14, 16 have been distracted relative to each other, the clip 10 is advanced over a tissue such that the cutting blade 38 of the clip 10 incises the tissue. Once the tissue has been incised to a certain length, the arms 14, 16 can be released and the clip 10 can return to its biased closed state to ligate the incised tissue.

Embodiments of the surgical clip described above can be applied to a tissue using a variety of devices. FIGS. 4A-4E illustrate one exemplary embodiment of a clip applier device. As shown, the clip applier device 100 generally includes a housing 102 having a stationary handle 104 and a first movable handle or trigger 106 and a second movable handle or trigger 108 both of which are pivotally coupled to the housing 102 and biased in a first position, away from the stationary handle 104, via a biasing spring 109. An elongate shaft 110 extends from the housing 102 and includes an end effector with a pair of opposed jaws 112 formed on a distal end thereof for clamping tissue. The elongate shaft 110 can be rotatably coupled to the housing 102, and it can include a rotation knob 114 for rotating the shaft 110 relative to the housing 102. The clip applier 100 includes a jaw closure assembly 116, illustrated in an exploded view in FIG. 4C that controls the relative positioning of the opposed jaws 112, and a cartridge assembly 118, illustrated in an exploded view in FIG. 4D, that contains one or more surgical clips 10 and that operates in conjunction with the clip applier 100 to apply the surgical clips 10 to a tissue. The various components of the jaw closure assembly 116 and the cartridge assembly 118 will be described in more detail below.

Figure 4A:
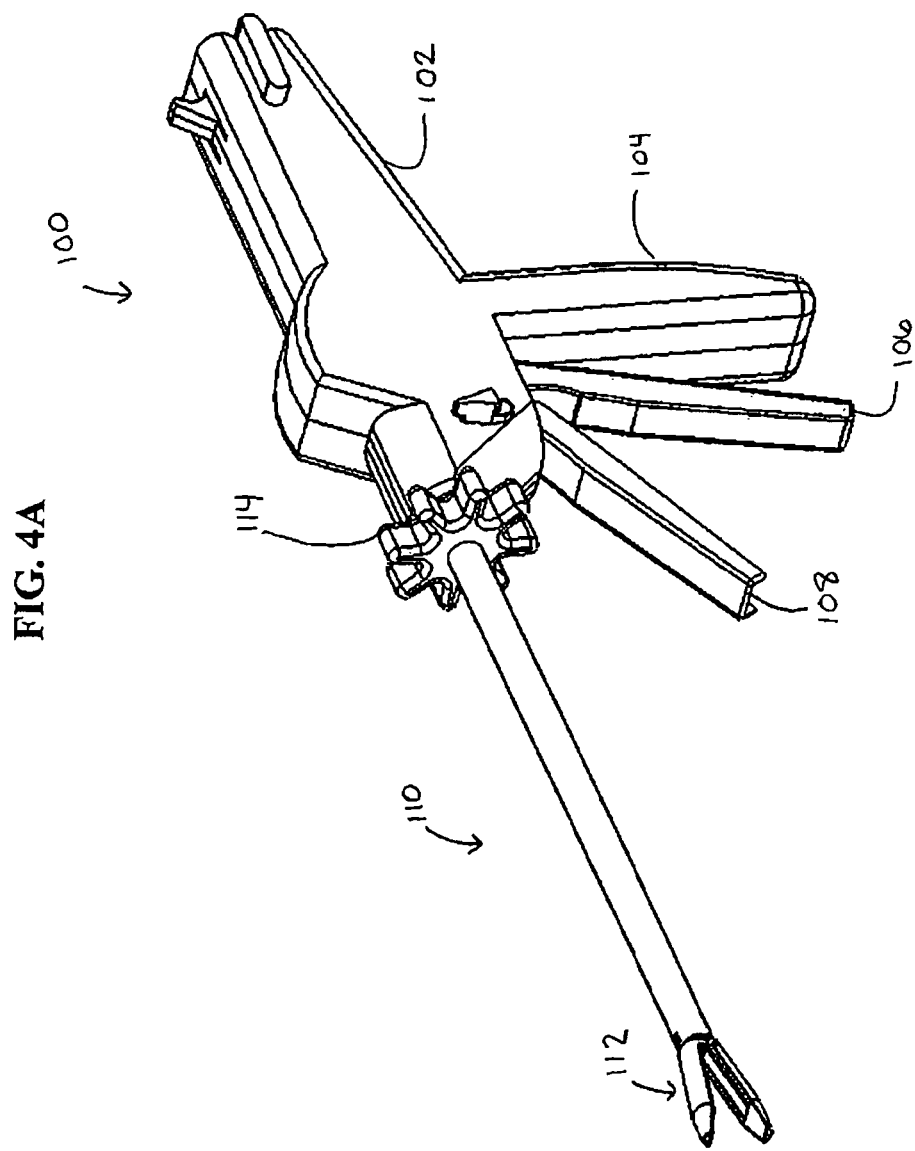
FIG. 4A is a perspective view of one embodiment of a surgical clip applier.
Figure 4B:
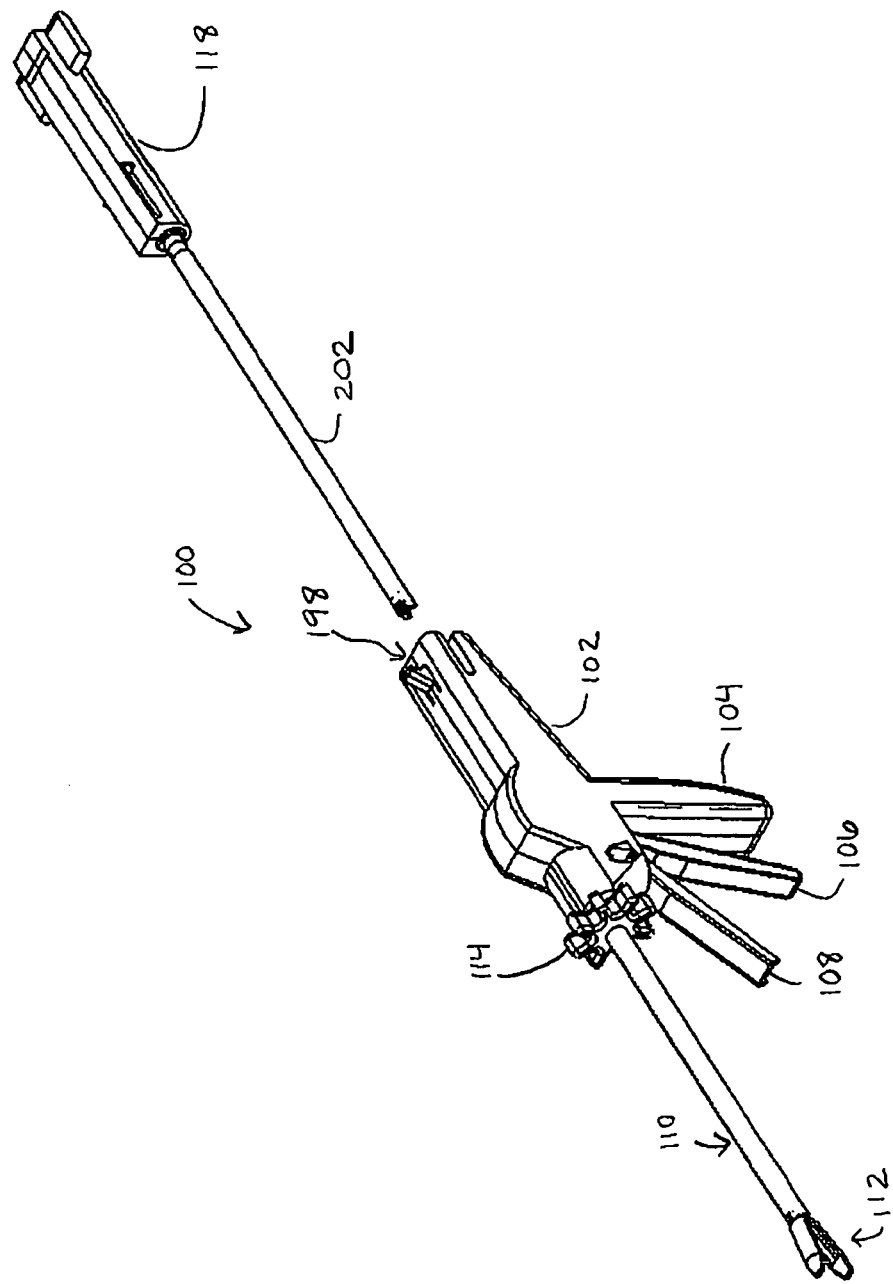
FIG. 4B is a perspective view of the surgical clip applier of FIG. 4A showing a cartridge assembly removed from the device.
Figure 4C:
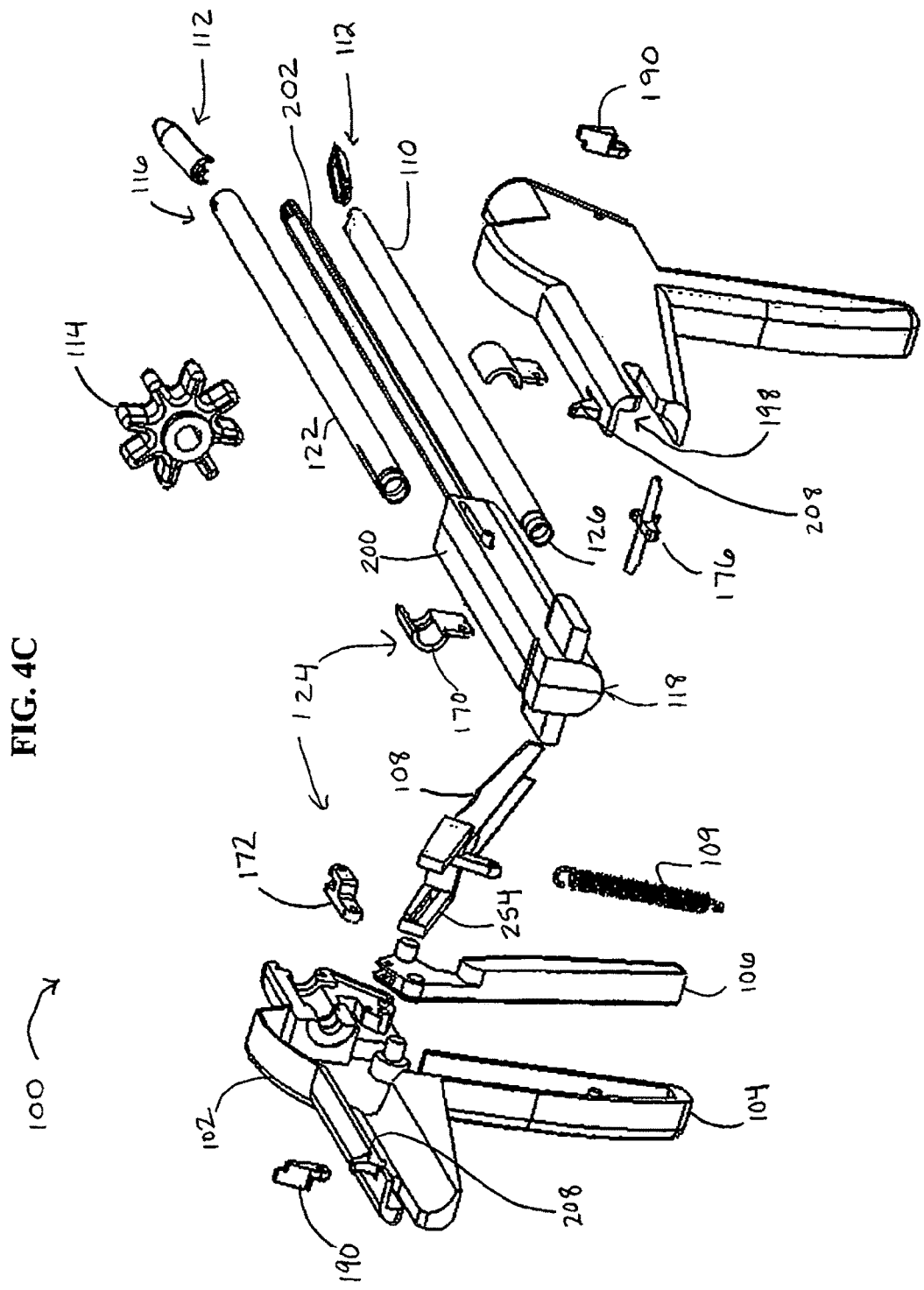
FIG. 4C is an exploded view of the clip applier of FIG. 4A.

FIG. 4C illustrates the various components of the jaw closure assembly 116 that can be present in exemplary embodiments of a clip applier device. In general, the jaw closure assembly 116 includes an elongate retainer shaft 110 having a proximal end coupled to the housing 102 and a distal end having the opposed jaws 112 pivotally disposed thereon. A closure tube 122 is disposed along a length of the retainer shaft 110 and has a proximal end coupled to the first moveable handle 106 by a linkage assembly 124 and a distal end disposed in proximity to the opposed jaws 112. In use, actuation of the first moveable handle 106 moves the closure tube 122 along the retainer shaft 110 to either approximate the opposed jaws 112 for closure thereof or to distract and thus open the jaws 112.

The retainer shaft 110 can have a variety of configurations. In one exemplary embodiment, the retainer shaft 110 includes a lumen 126 extending along a length thereof. The lumen 126 is operable to receive a shaft portion 202 of the clip advancement assembly 118 such that the clips 10 carried by the cartridge assembly 118 can be disposed in proximity to the opposed jaws 112.

Figure 5A:
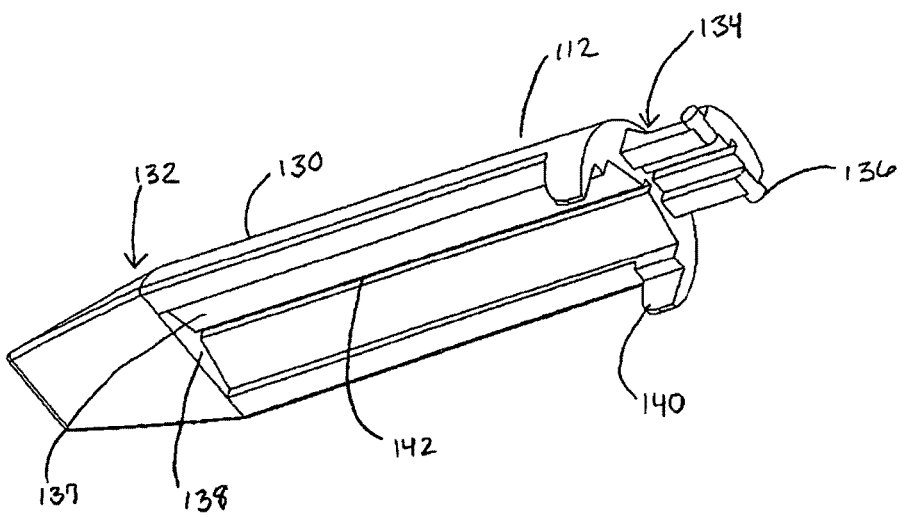
FIG. 5A is a perspective view of a jaw of the clip applier of FIG. 4A.
Figure 5B:
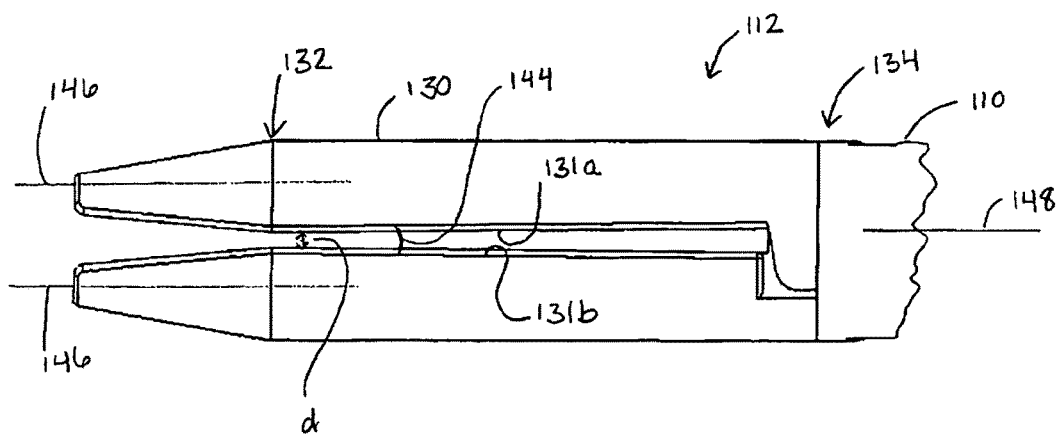
FIG. 5B is a side view of a pair of opposed jaws of the clip applier of FIG. 4A.

While the jaws 112 can have a variety of configurations, FIGS. 5A and 5B illustrate one exemplary embodiment thereof. As illustrated in FIG. 5A, each of the opposed jaws 112 can be formed of an elongate jaw body 130 having a coupling mechanism 136, such as a pin, that pivotally couples the jaw 112 to the retainer shaft 110. The jaws 112 can also include a variety of elements configured to work in conjunction with the cartridge assembly 118 to allow the clips 10 to be applied to tissue held between the jaws 112. For example, each jaw 112 can include clip guides 137, a clip stop element 138, and a tissue stop element 140. The clip guides 137 can extend between the distal and proximal ends 132, 134 of the jaws 112 and can allow clips 10 to be advanced between the jaws 112 when the jaws 112 are in a closed position. The clip stop element 138 can be disposed at a distal end 132 of the jaws 112 and, during operation, can limit the advancement of one or more clips 10 from the cartridge assembly 118 beyond the distal end of the jaws 112. The tissue stop element 140 can be disposed at a proximal end 134 of the jaws 112 and, during operation, can limit or prevent tissue held between the jaws 112 from entering the cartridge assembly 118. The jaws 112 can also be configured to allow for incision of issue disposed between the jaws. For example, a blade channel 142 can extend between the distal and proximal ends 132, 134 that, in use, can guide a cutting element from the cartridge assembly 118 and through a longitudinal axis of the jaws 112 to incise tissue disposed therebetween.

The jaws 112 also include opposed grasping surfaces 131a, 131b operable to contact and secure tissue disposed therebetween. While the opposed grasping surfaces can have a variety of configurations, in one embodiment, the grasping surfaces 131a, 131b can be angled relative to each other to effect a desired application. For example, as shown in FIG. 5B, the opposed grasping surface 131a, 131b can be oriented at an angle relative to each other such that a distance d between the opposed surfaces 131a, 131b increases from a distal portion 132 to a proximal portion 136 along a length of the jaws 112. In use, when tissue is clamped between the jaws 112, with such an angle formed between the opposed grasping surface 131a, 131b, a degree of compression of the tissue near the distal portion 132 is greater than a degree of compression of the tissue near the proximal portion 136, thereby limiting the ability of the tissue to slide from the distal end of the jaws 112.

Figure 6A:
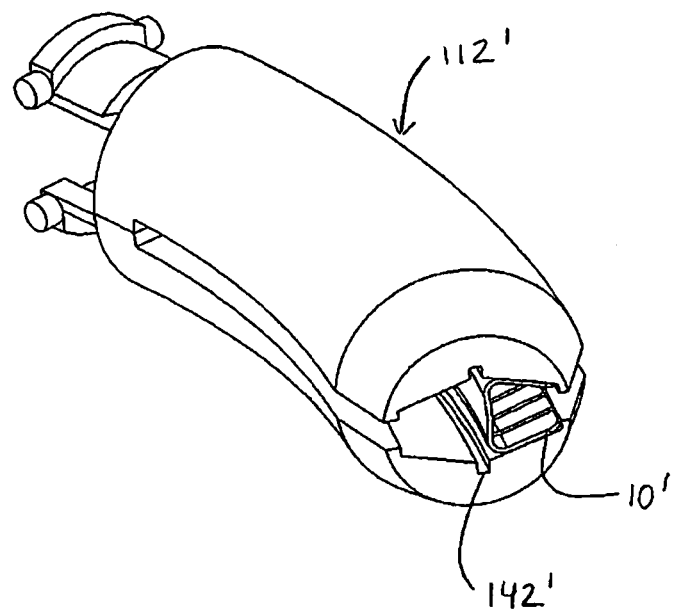
FIG. 6A is a perspective view of an alternate embodiment of the opposed jaws of FIG. 5B.
Figure 6B:
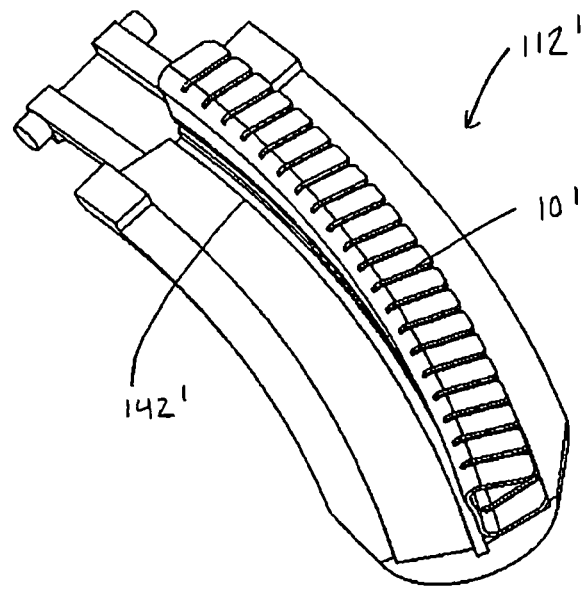
FIG. 6B is a perspective view of one of the opposed jaws of FIG. 6A.

One skilled in the art will understand that the opposed jaws 112 can have a variety of geometric configurations. In the embodiment illustrated in FIGS. 5A and 5B, each of the opposed jaws 112 have a longitudinal axis 146 that is substantially parallel to a longitudinal axis 148 of the elongate shaft 110. In an alternate embodiment, as illustrated in FIGS. 6A and 6B, the opposed jaws 112' can form an arc relative to a longitudinal axis of the elongate shaft 110. The curved shape of the jaws 112' and the curved shape of the blade channels 142' can force a clip 10' and a cutting element (not shown) to follow the arc shape when exiting the cartridge assembly 118. As such the curved jaws 112' can incise and apply clips 10' to a tissue along a curved path.

Figure 7:
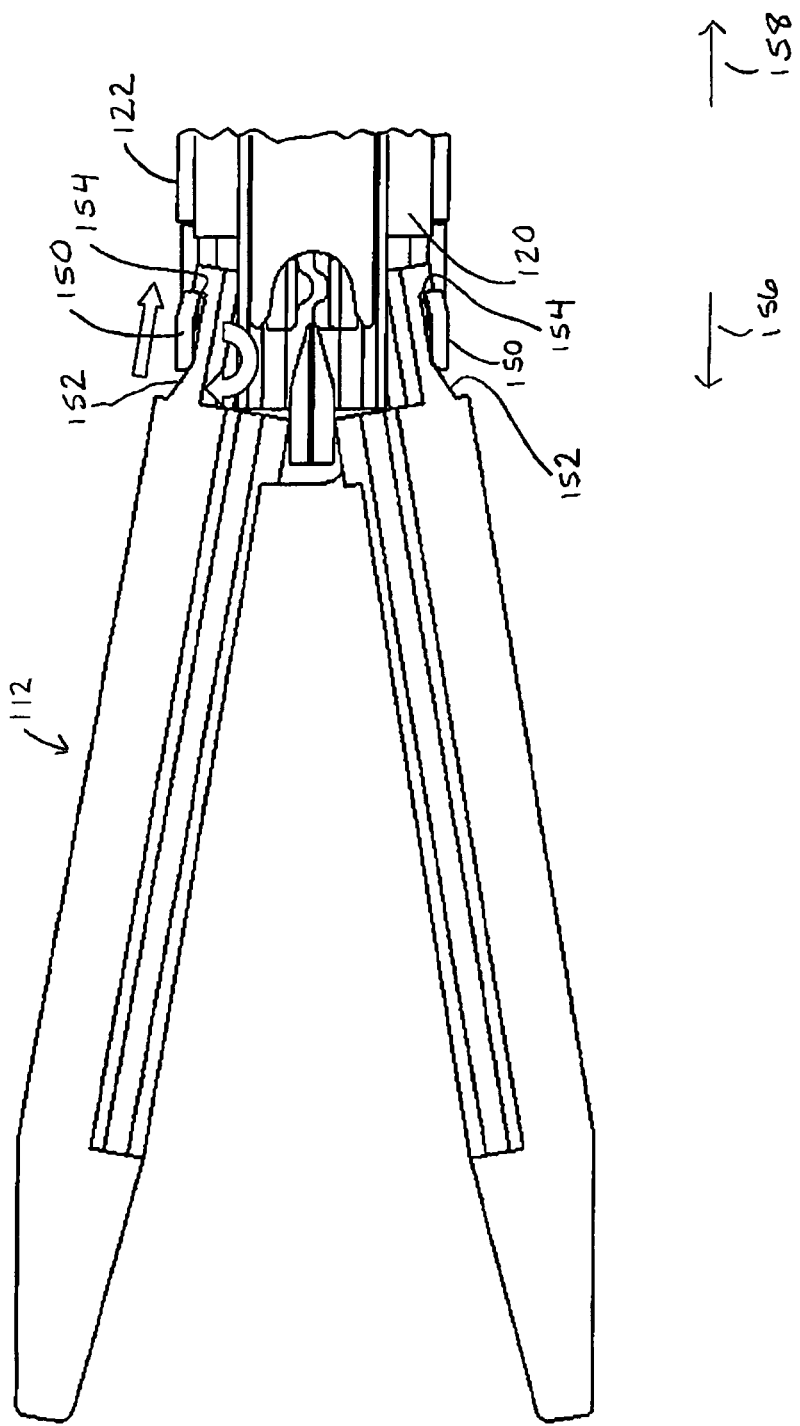
FIG. 7 is a sectional side view of the opposed jaws and jaw closure assembly of the clip applier of FIG. 4A.

As indicated above, the closure tube 122 can be used to effect opening and closing of the jaws 112. While the closure tube can have a variety of configurations to cause such motion of the jaws 112, FIG. 7 shows an exemplary embodiment of the closure tube 122 having crimp elements 150 disposed between cam surfaces 152 and a latch surface 154 of the jaws 112. In use, as the closure tube 122 is moved in a distal direction, indicated by arrow 156, each crimp element 150 slides over the cam surfaces 152 of the respective jaws 112 and causes the opposed jaws 112 to rotate toward each other to a closed position. As the closure tube 122 is moved in a proximal direction, as indicated by arrow 158, the crimp elements 150 engage the latch surfaces 154 of the jaws 112 and cause the opposed jaws 112 to rotate away from each other to an open position.

Referring again to FIG. 4C, the linkage assembly 124 couples the proximal end of the closure tube 122 to the first moveable handle 106. One skilled in the art will understand that the linkage assembly 124 can have a variety of configurations. In one exemplary embodiment, as shown in FIGS. 4C and 8A-8F, the linkage assembly 124 can include a closure yoke 170 that couples to the proximal end of the closure tube 122, a closure link 172 that couples the closure yoke 170 to the first moveable handle 106, and a locking mechanism 176 disposed in proximity to the closure yoke 170 and the closure link 172.

Figure 8A:
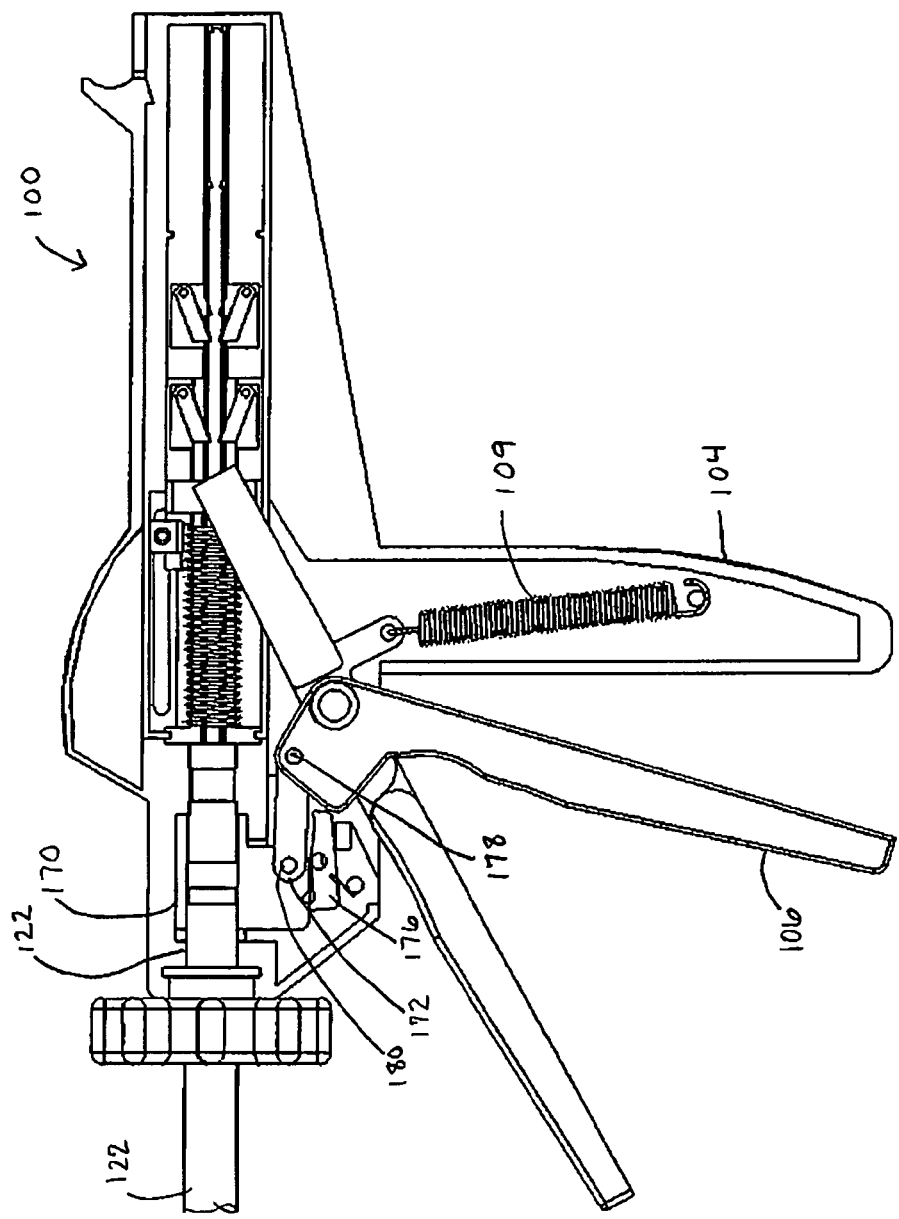
FIG. 8A is a sectional side view of the moveable handle and jaw closure assembly of the clip applier of FIG. 4A in a resting state.
Figure 8B:
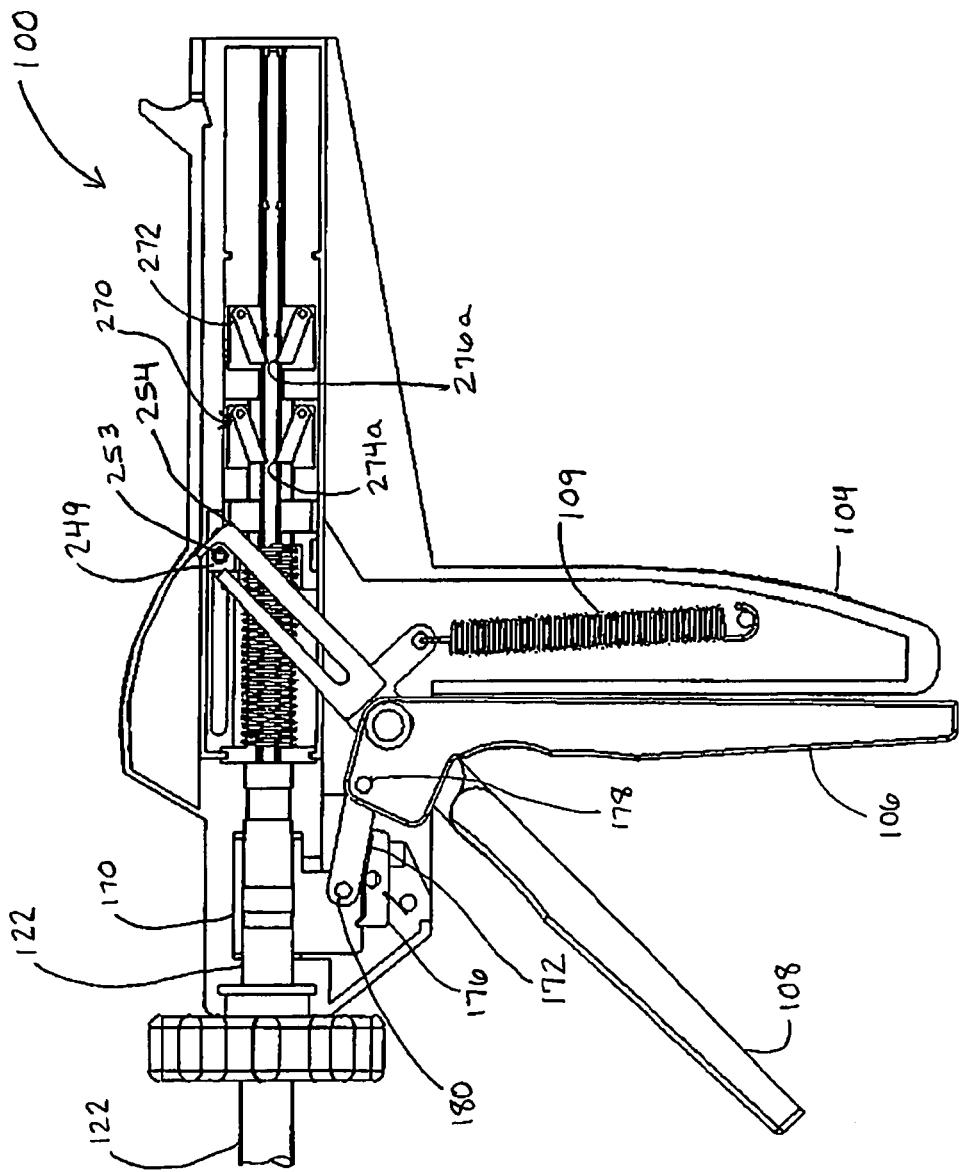
FIG. 8B is a sectional side view of the moveable handle and jaw closure assembly of FIG. 8A in an engaged state.

The closure link 172 is operable to convert rotational movement of the first moveable handle 106 to linear movement of the closure yoke 170. For example, the closure link 172 can be pivotably attached to the moveable handle 106 via a first pin 178 and can be pivotably attached to the closure yoke 170 via a second pin 180. In use, as the first moveable handle 106 is rotated toward the stationary handle 104 from an open position, as shown in FIG. 8A, to a closed position, as shown in FIG. 8B, the closure link 172 rotates about the pins 178, 180 and moves the closure yoke 170 toward the distal end of the device 100. As a result of such movement, the closure yoke 170 advances the closure tube 122 along the retainer shaft 110 to close the jaws 112 and clamp tissue disposed therebetween.

Figure 8D:
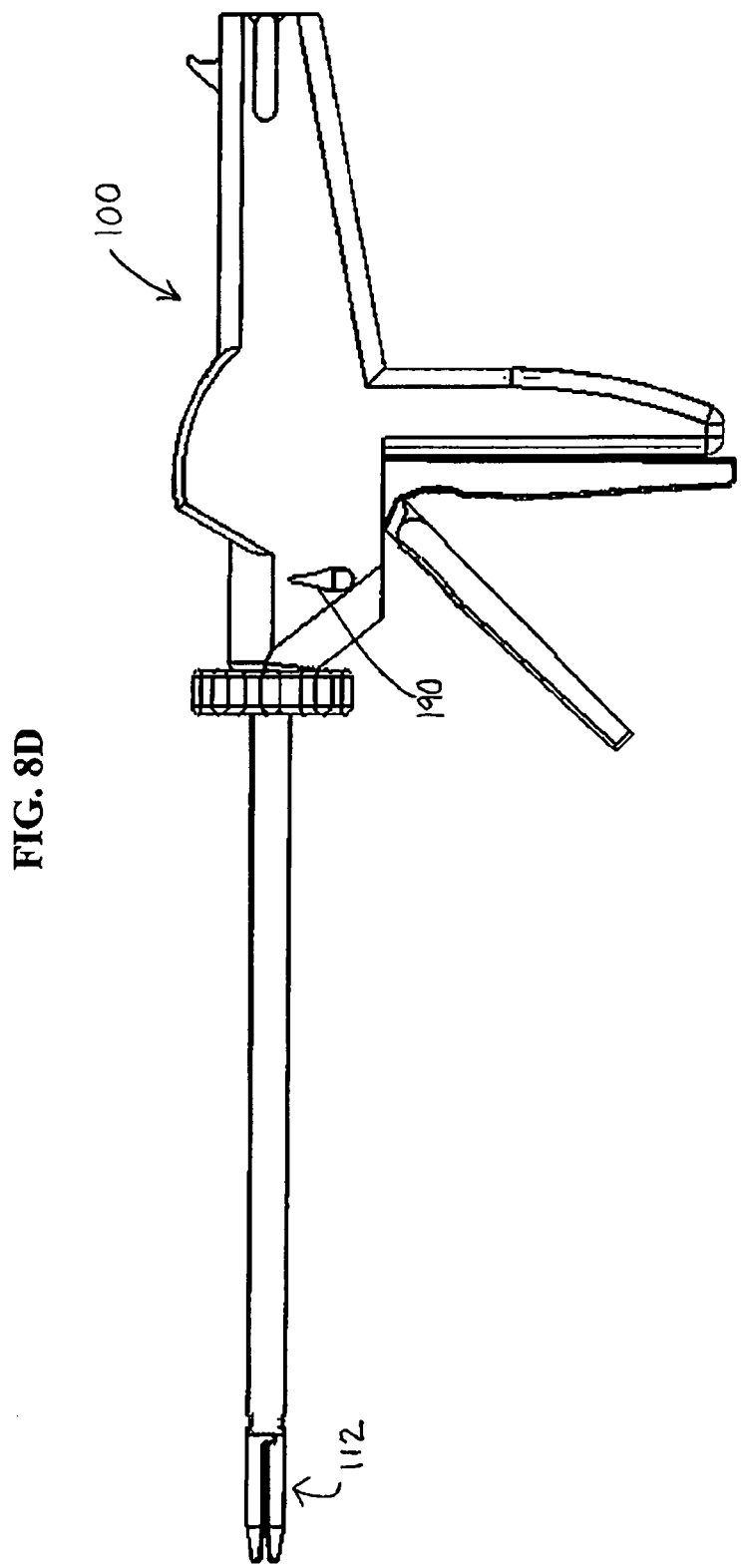
FIG. 8D is a side view of the clip applier of FIG. 4A with the opposed jaws positioned in a closed state.

When the jaws 112 are engaged in the closed position, the locking mechanism 176 can secure the positioning of the closure yoke 170 and closure tube 122 to maintain the clamped tissue between the opposed jaws 112. For example, as illustrated in FIG. 8C, the locking mechanism 176 can be pivotably coupled to the housing 102 via a pin 182 and can include a latching element 182 that is matable with a notch 186 of the closure yoke 170 and a spring element 186 that biases the locking mechanism 176 against the closure yoke 170. Returning to FIG. 8A, to engage the locking mechanism 176, as the closure link 172 moves the closure yoke 170 and closure tube 122 toward the jaws 112, the closure link 172 aligns the notch 186 of the closure yoke 170 with the latch element 184 of the locking mechanism 176. With such alignment, as shown in FIG. 8C, the spring element 188 causes the locking mechanism 176 to rotate about the pin 182 in a clockwise direction 189 such that the latch element 184 of the locking mechanism 176 engages the notch 186 of the closure yoke 170. As a result, the locking mechanism 176 can secure the position of the closure yoke 170 and closure tube 122 within the housing 102 to secure the opposed jaws 112 in a closed position, as shown in FIG. 8D.

Figure 8E:
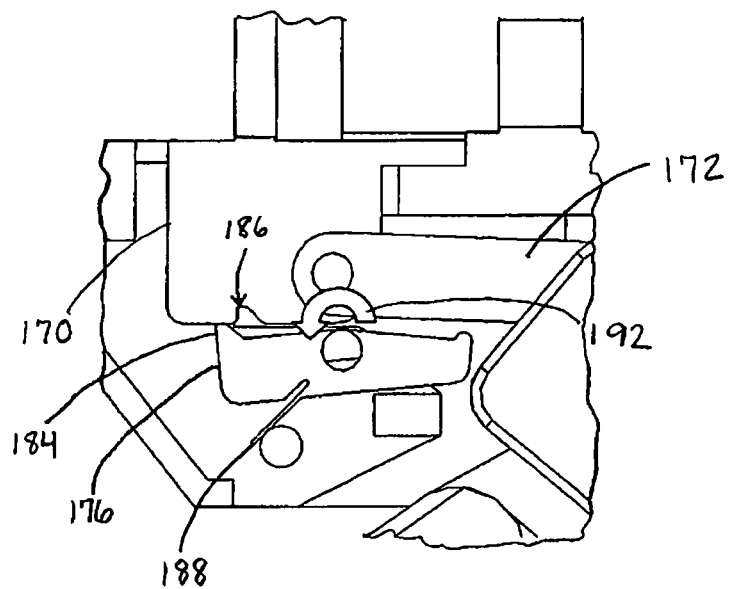
FIG. 8E is a side view of a locking mechanism of the jaw closure assembly of FIG. 8B in a disengaged state such that the opposed jaws can be positioned in an opened state.
Figure 8F:
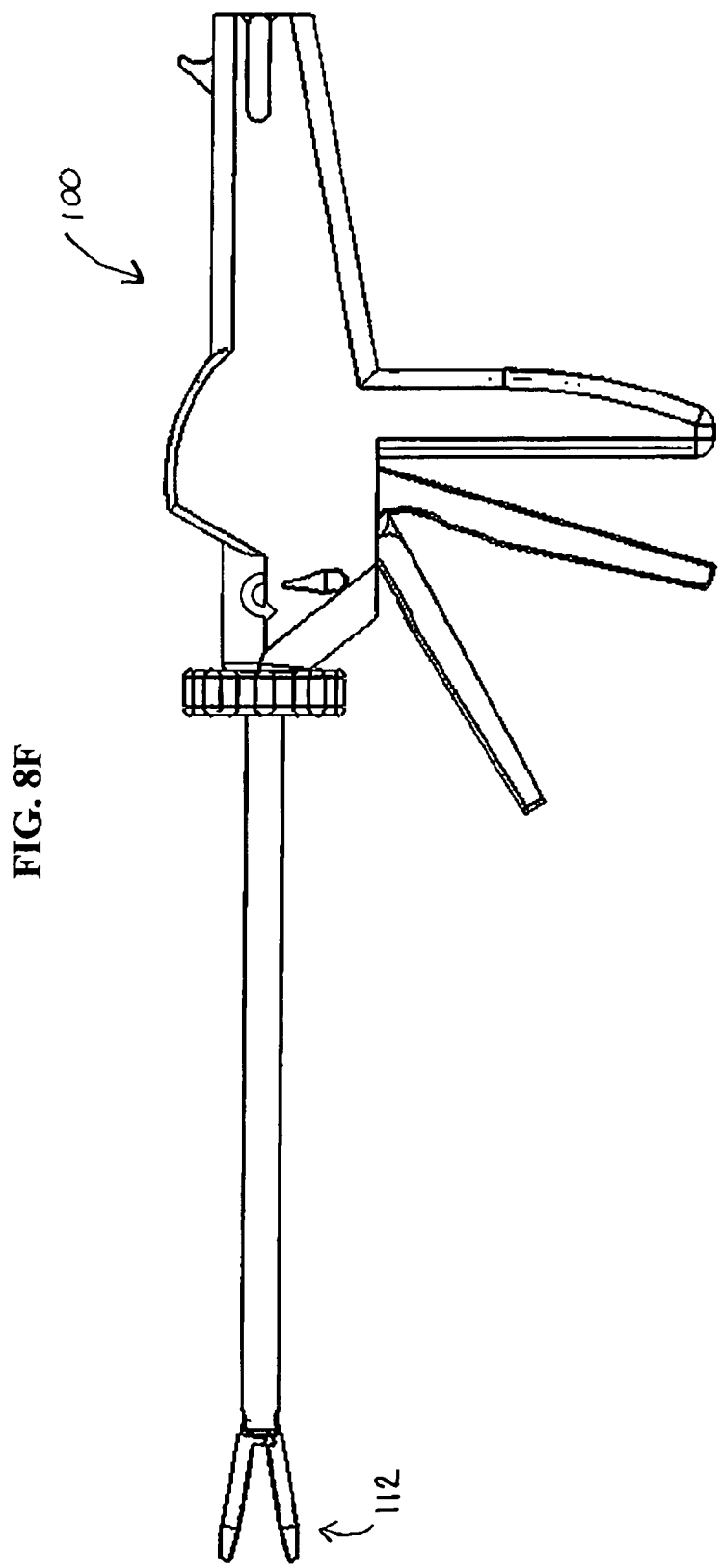
FIG. 8F is a side view of the clip applier of FIG. 4A with the opposed jaws in an opened state.

The locking mechanism 176 can also be disengaged from the closure yoke 170 to release the closure yoke 170 and closure tube 122 and to allow the jaws 112 to return to an open position. For example, the locking mechanism 176 can include a release lever 190 used to apply a torsional load to the locking mechanism 176. As shown in FIGS. 8E and 8F, a torsional load applied by the release lever 190 to the locking mechanism 176 in a counterclockwise direction causes the locking mechanism 176 to rotate along direction 192 and disengage the latch element from the notch 186 of the closure yoke 170. As a result, the handle 106 can return to its resting state via spring 109 and the handle 106 can pull the link 172 and closure yoke 170 proximally within the housing 102. The closure yoke 170, in turn can pull the closure tube 122 proximally thereby releasing the opposed jaws 112 and allowing the jaws 112 to return to an open position, as shown in FIG. 8F.

As indicated above, the cartridge assembly 118, contains one or more surgical clips 10 and operates in conjunction with the clip applier 100 to apply the surgical clips 10 to a tissue. FIGS. 4B-4E illustrate an exemplary embodiment of the cartridge assembly 118 which, in general, includes a housing 200 and an elongate shaft 202 extending from the housing 202, the elongate shaft 202 having a lumen 210 extending therethrough between a distal and proximal end. The cartridge assembly 118 houses surgical clip supply 10, an elongate cutting element or blade 238 extending along a length of the shaft 202 and an advancing assembly 204 that is operable to advance the blade 238 and the clips 10 into the opposed jaws 112 of the clip applier 100 to incise and ligate tissue disposed therein. The various components of the cartridge assembly 118 will be described in more detail below.

Figure 4D:
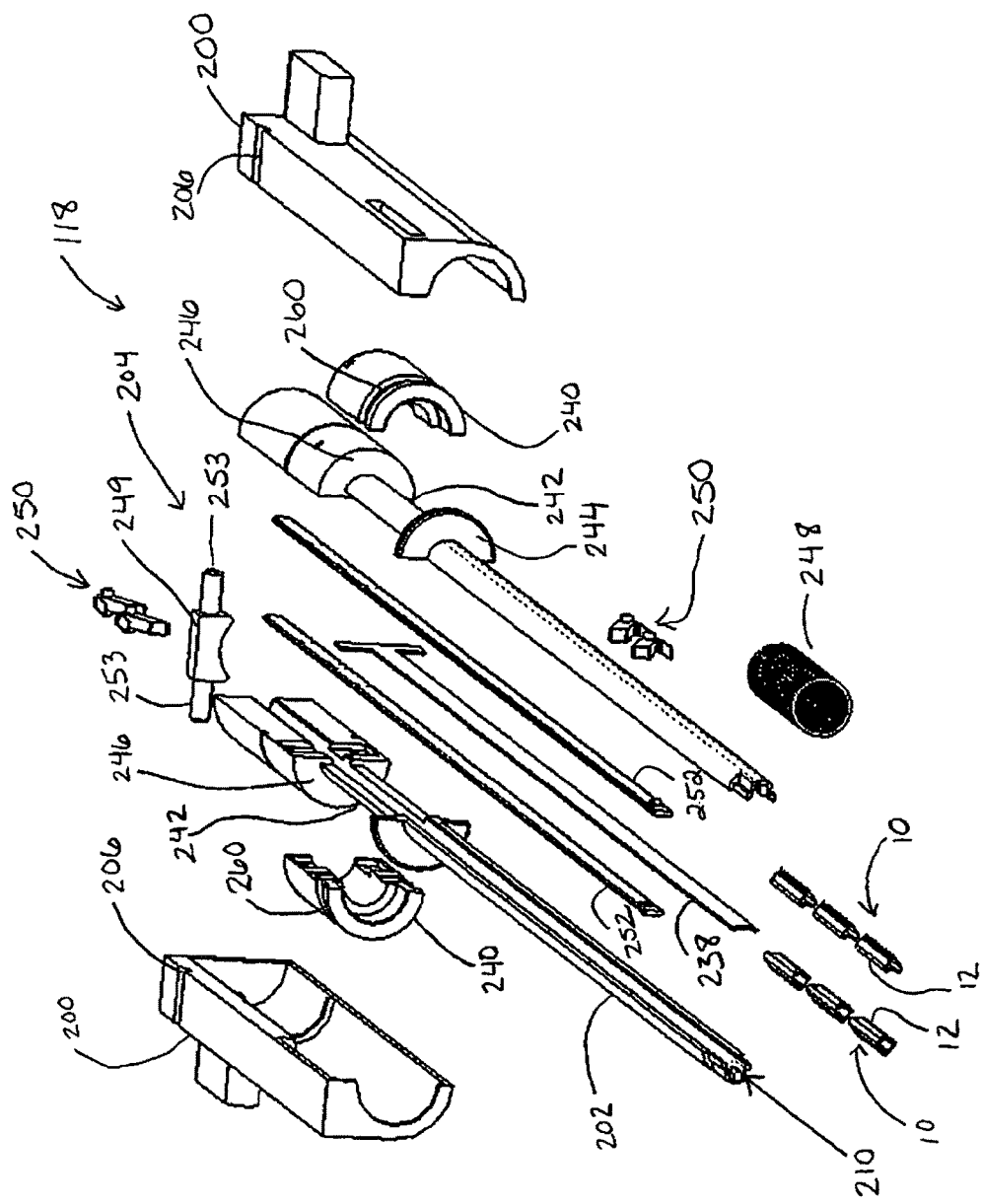
FIG. 4D is an exploded view of the cartridge assembly of FIG. 4B.

The housing 200 is configured to allow removable coupling of the cartridge assembly 118 to the housing 102 of the clip applier 100. For example, the housing 200 can include an attachment mechanism that secures the cartridge assembly 118 to the housing 102 of the clip applier 100. In particular, as shown in FIG. 4D, the housing 200 includes a notch 206 that mates with a latch 208 of the housing 102. When the cartridge assembly 118 is inserted within the housing 102, the latch 208 engages the notch 206 to secure the cartridge assembly 118 to the housing 102. When the latch 208 is disengaged from the notch 206, the cartridge assembly 118 can be decoupled and removed from the housing 102. While the cartridge assembly 118 can be inserted within the housing 102 in a variety of ways, in one embodiment as shown in FIG. 4B, the cartridge assembly 118 can be inserted within, or removed from, an opening 198 formed in a proximal end of the applier 100 the clip applier 100. As such, one or more cartridge assemblies 118 can be inserted or removed from the device 100 while the elongate shaft 110 of the device 100 is maintained within a trocar or patient.

The elongate shaft 202 can be inserted within the lumen 126 of the retainer shaft 110 such that a distal end of the elongate shaft 202 is disposed in proximity to the opposed jaws 112. The elongate shaft 202 can also have one or more clips 10 and the blade 238 disposed within the elongate shaft lumen 210 for delivery to the opposed jaws 112 of the device 100.

One skilled in the art will understand that the clip supply 10 and the clips thereof can be arranged within the shaft lumen 210 in a variety of ways. For example, multiple clip supplies 10 can be aligned end-to-end such that a longitudinal axis of each clip 10 is substantially parallel to a longitudinal axis of the elongate shaft 202. In another example, as illustrated in FIG. 4C, the clip supplies 10 can be arranged in pairs on either side of the blade 238 along a length of a lumen 210 such that the spines 12 of opposed clip supplies 10 face each other. In such an arrangement, which is particularly useful for transection, as the blade 238 incises tissue disposed within the jaws 112 into two separate tissue portions, the clip supply pair can be applied to the separate tissue portions at substantially the same time. While FIG. 4D illustrates the elongate shaft 202 to include three pairs of clip supplies 10, one skilled in the art will understand that any number of clips or clip supplies can be disposed within the shaft lumen 210.

One skilled in the art will further understand that the clips of the clip supply can be stored within the lumen 210 of the elongate shaft 202 in either a closed or a opened position. Clips formed from a spring material, such as a spring steel, can be stored in the in the lumen 210 in a closed position to maintain the spring properties of the clip and to minimize excessive straining of the arms 14, 16 prior to application to a tissue. Additionally, clips formed from a superelastic material, such as nitinol, can be stored in the in the lumen 210 in an opened state. In either case however, prior to delivery of a clip to a tissue for application thereto, the clip should be opened to allow the arms 14, 16 of the clip 10 to be disposed on either side of a tissue to be ligated. As such the cartridge assembly 118 can include a clip opening mechanism 220 that maintains the clip in an open state as the clip is delivered to a tissue.

Figure 9A:
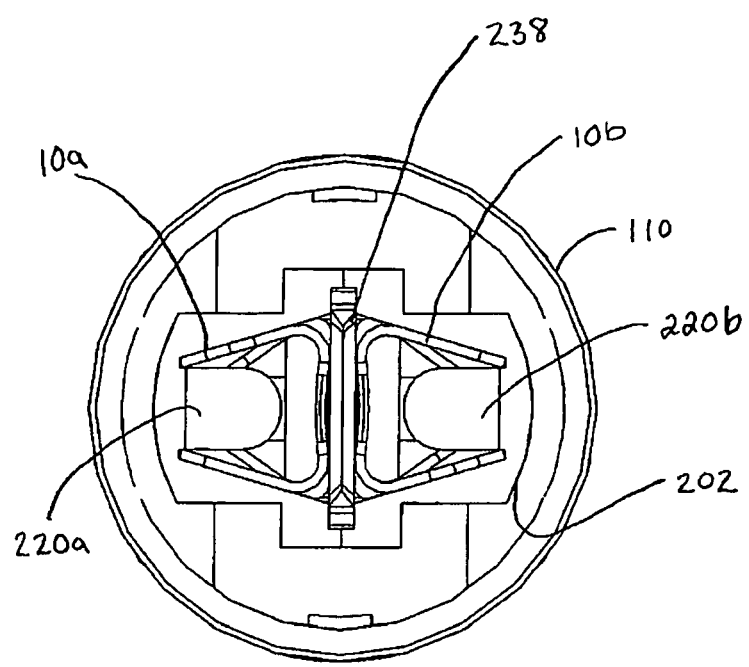
FIG. 9A is an end view of the clip applier of FIG. 4A having a clip opening mechanism disposed therein.
Figure 9B:
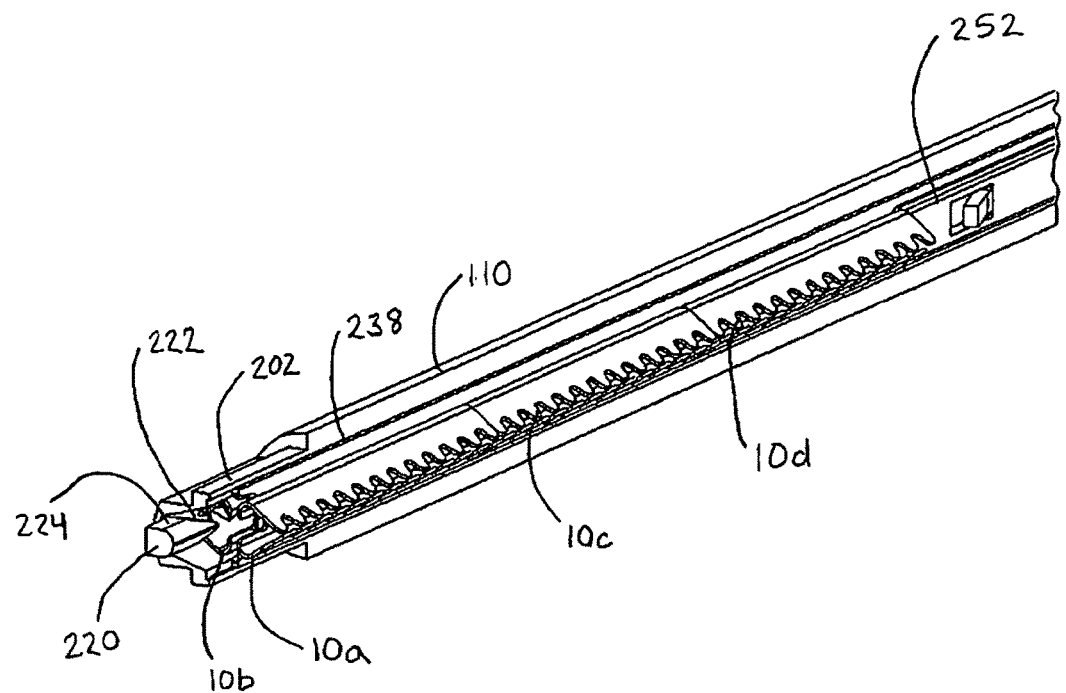
FIG. 9B is a cross-sectional perspective view of a distal end of the cartridge assembly of FIG. 4A.
Figure 9C:
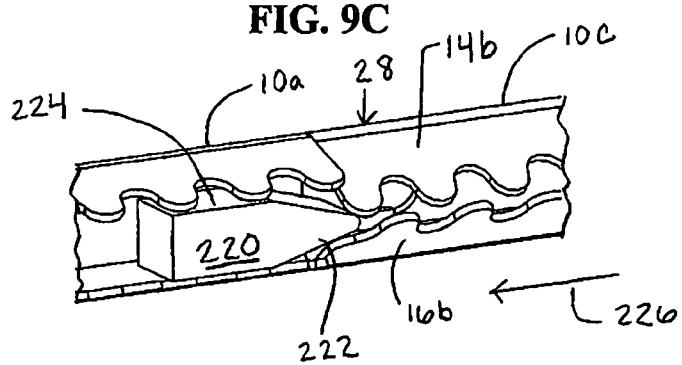
FIG. 9C is a perspective view of a clip being advanced toward the clip opening mechanism of FIGS. 9A and 9B.
Figure 9D:
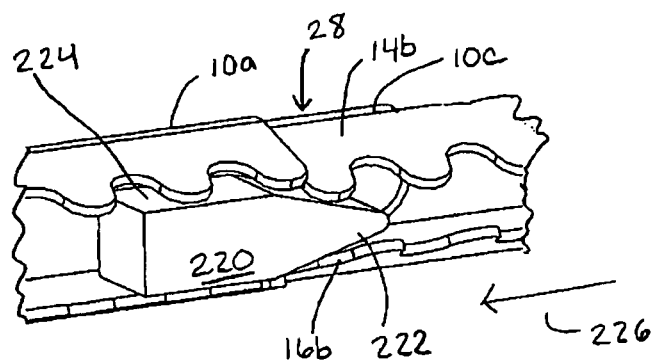
FIG. 9D is a perspective view of the clip being further advanced over the clip opening mechanism of FIG. 9C.
Figure 9E:
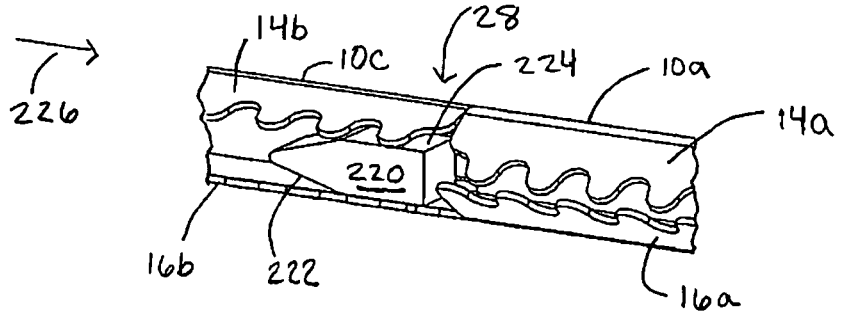
FIG. 9E is a perspective view of the clip fully advanced over the clip opening mechanism of FIG. 9C.

FIGS. 9A-9E illustrate one embodiment of the clip opening mechanism 220 that is operable to expand the arms 14, 16 of a clip from a biased closed position to an open position, thereby allowing the clip 10 to be applied to a tissue. As illustrated in FIG. 9B, the clip opening mechanism 220 is coupled to a distal end of the elongate shaft 202 in proximity to opposed jaws of the clip applier, and the clip opening mechanism 220 includes a wedge portion 222 and an elongated portion 224. In use, as shown in FIG. 9C, a clip 10c disposed within the elongate shaft 202 in the closed position is urged toward the wedge portion 222 of the clip opening mechanism 220 along direction 226. As shown in FIG. 9D, as the clip 10c is moved along the direction 226, the wedge portion 22 inserts between the arms 14b, 16b at the first end 28 of the clip 10c to force the arms 14b, 16b apart. As the clip 10c is further moved along the direction 226 the wedge portion 22 continues to separate the arms 14b, 16b of the clip 10c until the clip 10c reaches the elongate portion 224, as shown in FIG. 9E, The elongate portion 224 maintains the arms 14b, 16b in a spaced-apart relationship as the clip 10c continues to move in the direction 226, towards opposed jaws 112. As the clip 10c enters the jaws 112 of the device 100, the arms 14b, 16b can be disposed on either side of tissue clamped by the jaws 112. When the clip 10c falls off the elongated potion 224, as shown by the clip 10a illustrated in FIG. 9E, the arms 14a, 16a return to a biased closed state to engage tissue disposed therebetween.

While FIGS. 9C-9E illustrate the use of a single clip opening mechanism 220, one skilled in the art will understand that the elongated shaft 202 can include any number of clip opening mechanisms. For example, as shown in FIG. 9A, the elongate shaft 202 includes a first and second clip opening mechanism 220a, 220b disposed on either side of a blade 238. In use, each of the clip opening mechanisms 220a, 220b opens corresponding clips 10a, 10b of a pair of opposed clips, thereby allowing delivery of each of opened clips to a corresponding, separate tissue portion disposed within the jaws of the clip applier.

Figure 10A:
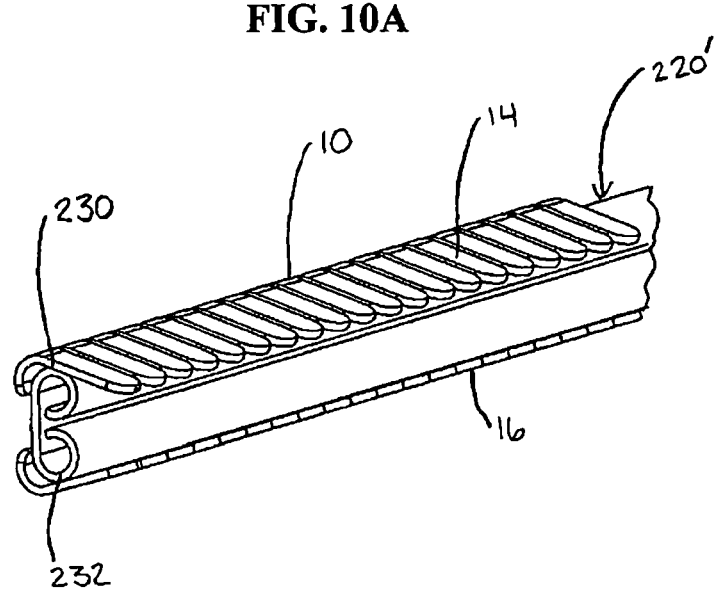
FIG. 10A is a perspective view of an alternate embodiment of a clip opening mechanism disposed within a clip.
Figure 10B:
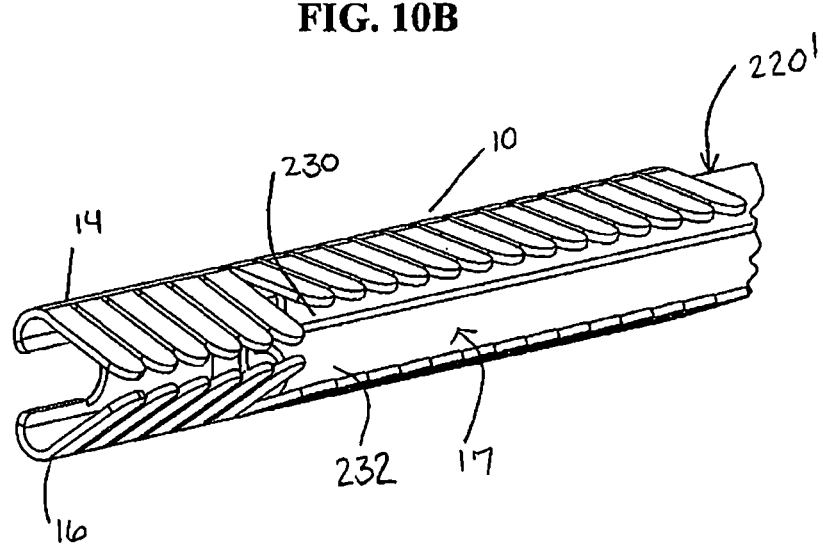
FIG. 10B is a perspective view the clip opening mechanism of FIG. 10A being withdrawn from the clip.

FIGS. 10A-10B illustrate another embodiment of a clip opening mechanism 220' that is operable to maintain a clip 10 in an open position within the elongate shaft 202, prior to delivery to a tissue. For example, the clip opening mechanism 220' can include first and second arm extension portions 230, 232. When inserted between the arms 14, 16 of a clip 10, the first and second arm extension portions 230, 232 force the arms 14, 16 apart from each other and maintain the arms 14, 16 in a spaced-apart relationship. In one embodiment, the clip opening mechanism 220' is coupled to the advancing assembly 204 such that the clip opening mechanism 220' can translate along a longitudinal axis of the elongate shaft 202 with the clip 10 as the advancing assembly 204 moves the clip 10 into the opposed jaws 112. In such a configuration, the clip opening mechanism 220' can maintain the arms 14, 16 of the clip 10 in an open position while the clip 10 is inserted into the opposed jaws 112. Once the clip 10 is inserted in the opposed jaws 112, the advancing assembly 204 can retract the clip opening mechanism 220' from the clip 10, as shown in FIG. 10B, to allow the arms 14,16 to return to their biased closed state and ligate tissue held within the opposed jaws 112 and disposed within the channel 17 of the clip 10.

Figure 4E:
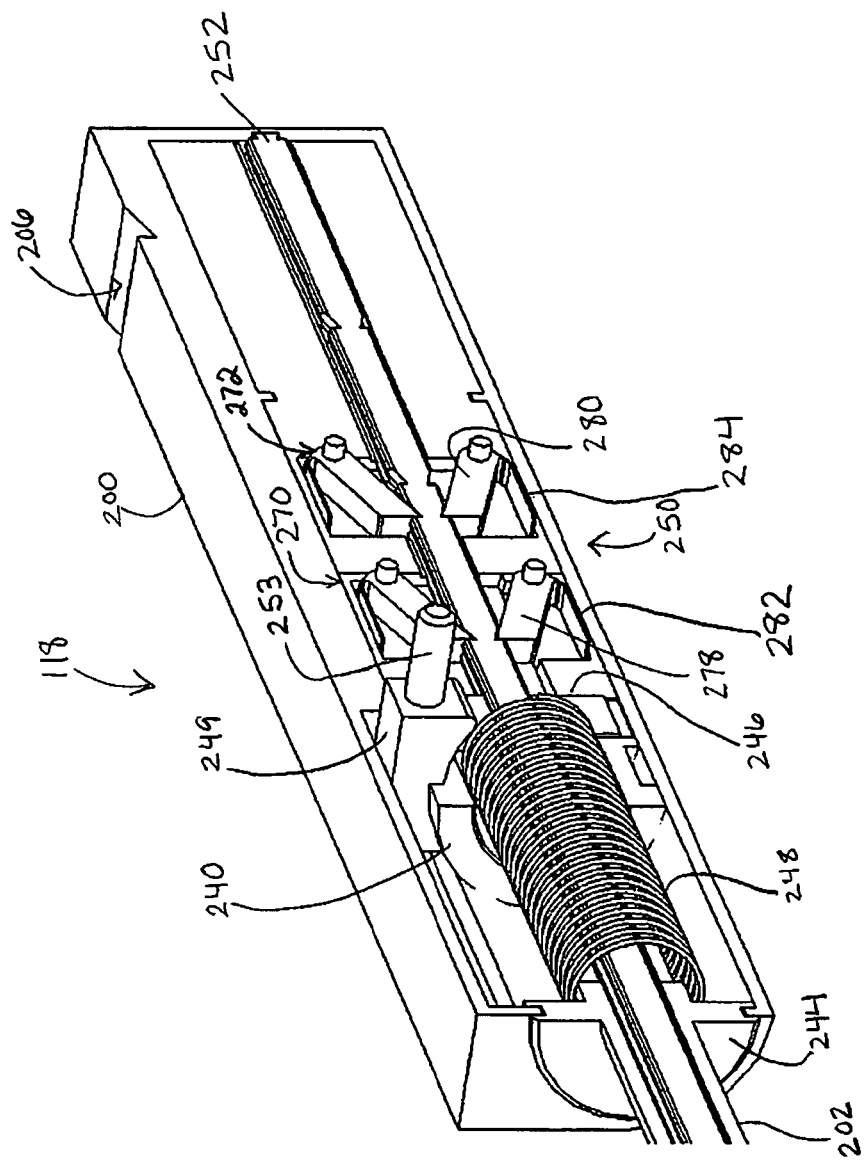
FIG. 4E is a cut-away view of a proximal portion of the cartridge assembly of FIG. 4C.

Returning to FIGS. 4A-4E, the advancing assembly 204, as indicated above, operates in conjunction with the clip applier 100 to advance the blade 238 and clips 10 into the opposed jaws 112 of the clip applier 100 to incise and ligate tissue disposed therein. As illustrated in FIGS. 4D and 4E an exemplary embodiment of the advancing assembly 204 includes an advancer 240 having one or more pusher bars 252 and the blade 238 coupled thereto. The advancer 240 can be slidably disposed on a portion 242 of the elongate shaft 202 between first and second walls 244, 246 and a spring 248 can be disposed between the advancer 240 and the first wall 244 to bias the advancer 240 toward a proximal end of the cartridge 118 in a rest state. The advancer 240 also couples to the second moveable handle 108 such that, in use, when the second moveable handle 108 is rotated toward the stationary handle 102 to overcome a force exerted by the spring on the advancer 240, the handle 108 moves the advancer 240 toward the distal end of the cartridge 118. As a result of such motion, the advancer 240 causes the blade 238 to move from a retracted position within the elongate shaft 202 to an extended position within the opposed jaws 112 and causes the pusher bars 252 to dispense one or more clips from the distal end of the cartridge 118 to the opposed jaws 112, thereby incising and ligating tissue clamped therebetween.

Figure 11:
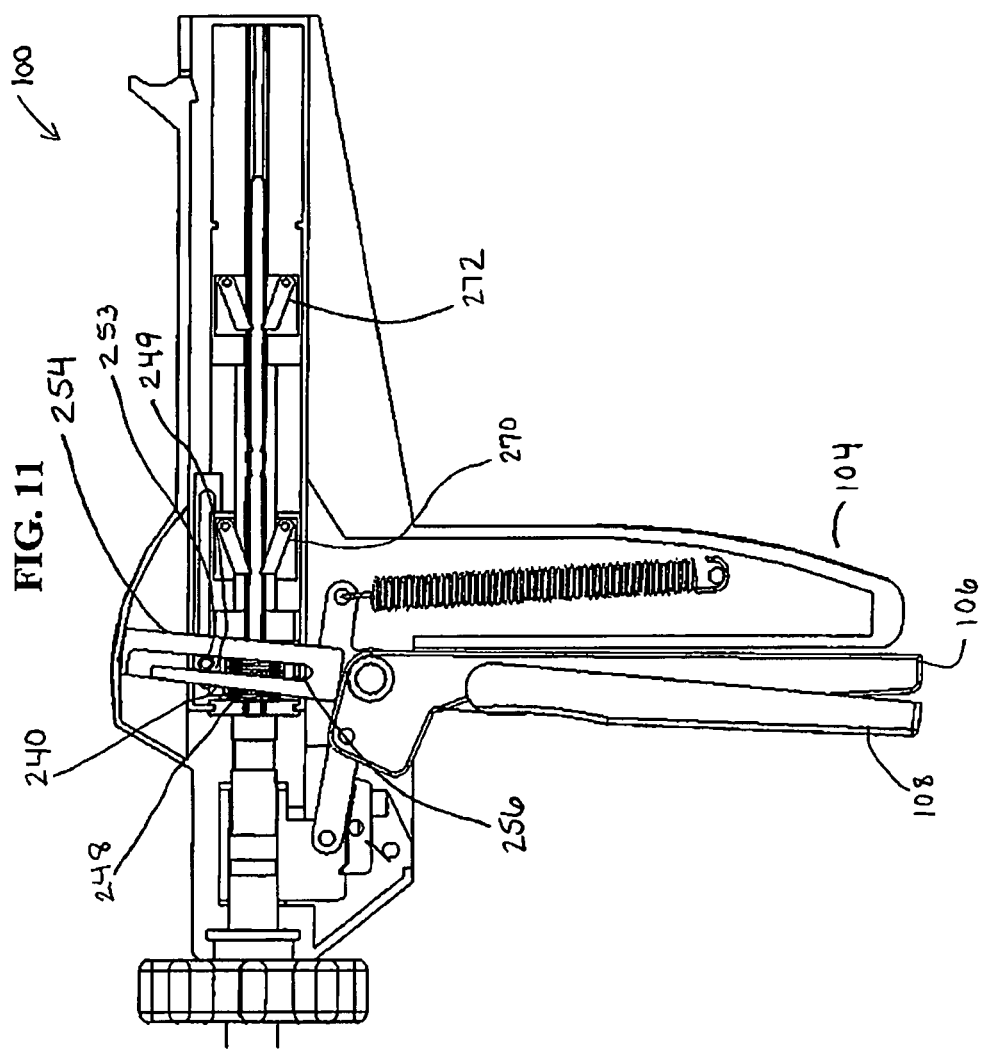
FIG. 11 is a cross-sectional side view of a proximal end of the clip applier of FIG. 4A after deployment of a clip from the cartridge assembly.

While one skilled in the art will understand that the advancer 240 can be coupled to the second moveable handle 108 in a variety of ways, in one exemplary embodiment, the advancer 240 can include a pusher block 249 which allows for selective coupling of the second moveable handle 108 and the advancer 240. For example, the pusher block 249 can include tabs 252 that can be selectively coupled with a pusher block coupling element 254 of the second handle 108 to effect movement of the advancer 240. In use, as indicated in FIG. 8B, when the first moveable handle 106 is rotated toward the stationary handle 104 to close the opposed jaws 112, it also rotates the second moveable handle 108 relative to the stationary handle 104 such that pusher block coupling element 254, such as a hook element, engages the tab 252 of the pusher block 249. As the second moveable handle 108 is then rotated toward the stationary handle 104, as shown in FIG. 11, the tab 252 travels within a slot 256 of the pusher block coupling element 254 and, as a result, causes the pusher block 249 and advancer 240 to move toward the distal end of the cartridge 118 and compress the spring 248. Conversely, as the second moveable handle 108 is released from the stationary handle 104, the spring 248 can expand and move the advancer 240 and pusher block 249 proximally to return the advancer 240 and pusher block 249 to the rest state within the housing 200.

One skilled in the art will understand that the pusher block 249 can be coupled to the advancer in a variety of ways. For example, returning to FIGS. 4D and 4E, the pusher block 249 can be inserted within an annular groove formed in an outer surface of the clip advancer. In such a configuration, the pusher block 249 allows the elongate shaft 202 and the advancer 240 to be rotated within the cartridge housing 200 while maintaining a coupling between the advancer 240 and second moveable handle 108.

Figure 12A:
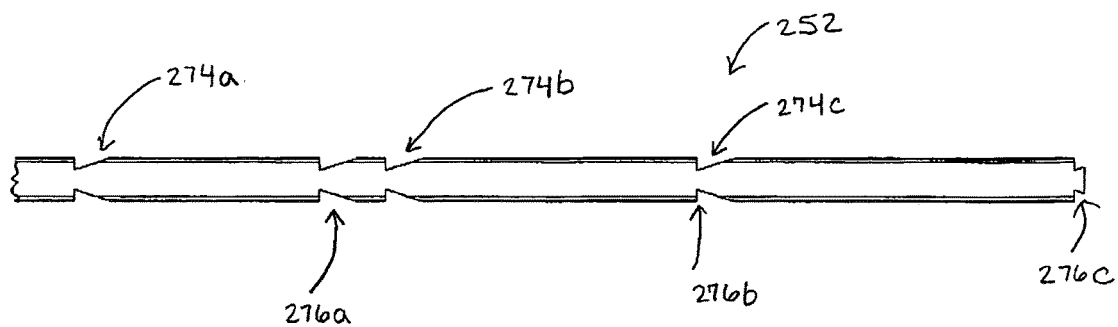
FIG. 12A is a side view of a proximal end of a pusher bar of the cartridge assembly of FIG. 4D.
Figure 12B:
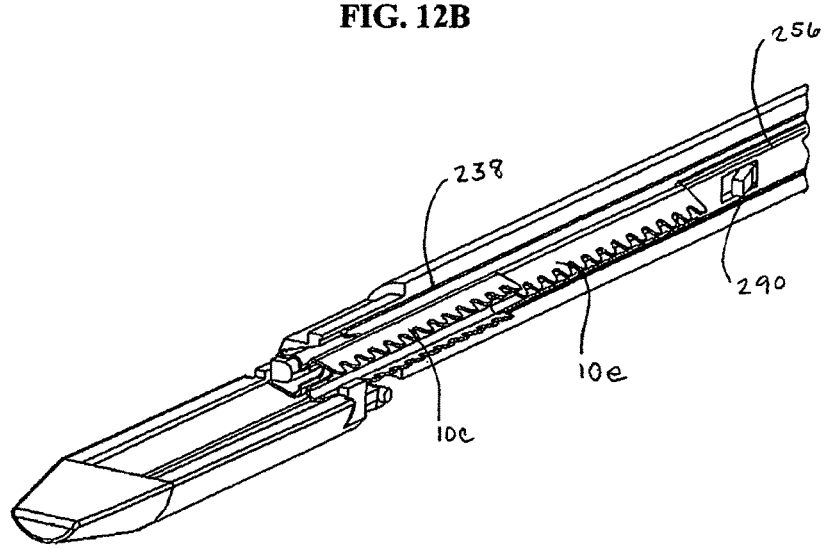
FIG. 12B is a perspective cut away view of a distal end of the cartridge assembly of FIG. 4D after firing of a clip.
Figure 12C:
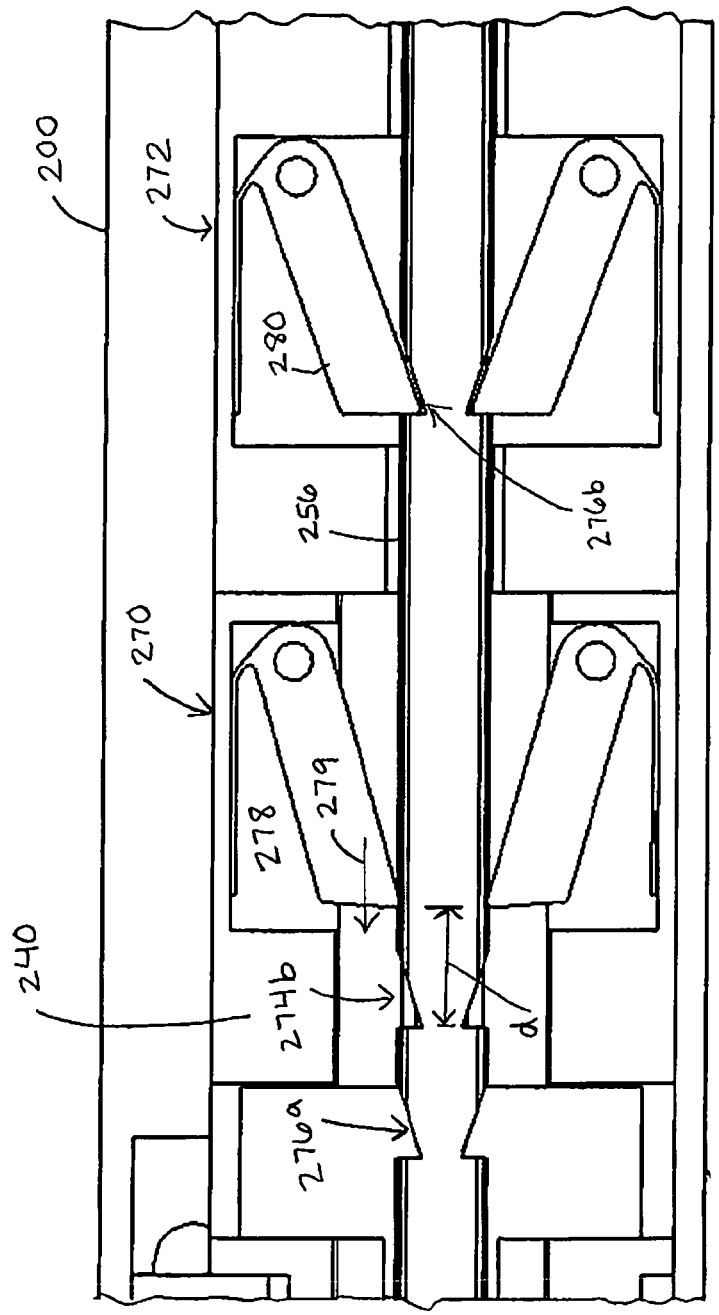
FIG. 12C is a cross-sectional side view of a ratchet assembly of the cartridge assembly of FIG. 4D.

The pusher bars 252 can extend within the elongate shaft 202 and include a distal end disposed in proximity to one or more clips 10 and a proximal end coupled to the advancer 240. While the proximal end of the pusher bars 252 can be coupled to the advancer 240 in a variety of ways, in one embodiment, the pusher bars 252 are coupled to a ratchet assembly 250 associated with the advancer 240 that allows the pusher bars 252 to be advanced within the elongate shaft 202 to deploy clips 10, disposed therein, in a serial manner. For example, the pusher bars 252, as shown in FIG. 12A, can include advancer notches 274a through 274c that selectively couple with an advancer ratchet 270 of the ratchet assembly 250 as shown in FIG. 12C. The pusher bars 252 also include brake notches 276a through 276c that selectively couple with a brake ratchet 272 of the ratchet assembly 250 as also shown in FIG. 12C. Returning to FIG. 4E, the advancer ratchet 270 is coupled to the advancer 240 and includes a ratchet lever 278 and spring element 282 that biases the lever 278 toward the pusher bar 256. The advancer ratchet 270 is operable to serially engage each of the advancer notches 274a through 274c of the pusher bar 252 to urge the pusher bar 252 toward the distal end of the cartridge assembly 118. The brake ratchet 272 is secured to the cartridge housing 200 and includes a ratchet lever 280 and spring element 284 that biases the lever 280 toward the pusher bar 252. The brake ratchet 272 is operable to serially engage the brake notches 276a through 276c in the pusher bar to limit or prevent the pusher bar 252 from moving in a proximal direction while applying a clip 10 to a tissue.

The following describes the use of the ratchet assembly 250 to provide serial deployment of a series of clips by the clip applier 100. In one embodiment as shown in FIG. 9B, the elongate shaft 202 includes a series of three clips 10a, 10c, and 10e disposed therein. In a rest state, before deployment, the distal most clip 10a is positioned in proximity to a clip opening mechanism 220 and the most proximal clip 10e is positioned in proximity to the distal end of the pusher bar 252. Also, in the rest state, the proximal end of the pusher bar 252, as shown in FIG. 8B, is coupled to the ratchet mechanism 250 such that the lever 278 of the advancer ratchet 270 is disposed within the first advancer notch 274a of the pusher bar 252 and the brake ratchet 272 is disposed within the first break notch 276a of the pusher bar 252.

After the first moveable handle 106 has been rotated toward the stationary handle 104 during a first firing procedure to activate the jaw closing assembly 116, the second moveable handle 108 can be rotated toward the stationary handle 104 as shown in FIG. 11, causing the advancer 240 to pull the advancer ratchet 270 toward the distal end of the cartridge 118. With such motion, the advancer 240 extends the blade 238 from the distal end of the cartridge 118 into the opposed jaws 112 and causes the advancer ratchet 270 to advance the pusher bar 252 toward the distal end of the cartridge assembly 118. As such, the pusher bar 252 contacts the proximal clip 10-5 and advances the series of clips 10a, 10c, 10e such that the distal clip 10a engages the clip opening mechanism 220 as shown in FIGS. 9C and 9D. Further motion of the pusher bar 252 in the distal direction advances the clip 10a into the opposed jaws 112 and causes the lever 280 of the brake mechanism 272 to engage the second brake notch 276b of the pusher bar 252, as shown in FIG. 12C. After the clip 10a has been delivered to the opposed jaws 112, the second clip 10c remains disposed on the clip opening mechanism 220.

As the second moveable handle 108 is released, the advancer 240 retracts the blade 238 from the opposed jaws 112. However, as illustrated in FIG. 12B, with such retraction, the distal end of the blade 238 is positioned behind the second clip 10c. To ensure that the cutting edge of the blade 238 is positioned in front of the second clip 10c during a subsequent firing procedure, thereby allowing tissue clamped between the jaws 112 to be incised just prior to delivery of the clip 10c, as the second moveable handle 108 is released, the advancer 240 moves the advancer ratchet 270 proximally within the housing 200 such that the lever 278 of the advancer ratchet 270 rest on the pusher bar 256 at a distance d from the second advancer notch 274b. As such, during a second firing procedure, when the second moveable handle 108 is rotated toward the stationary handle 104, the advancer 240 pulls the advancer ratchet 270 along the distance d along direction 279 while moving the blade 238 in a distal direction. While the advancer ratchet 270 is pulled along the distance d of the pusher rod 256, the advancer ratchet 270 does not cause the pusher rod 256 to advance the clips 10c, 10e. Instead, as the advancer ratchet 270 travels along the distance d, the advancer 240 aligns the blade 238 with the distal most clip 10c such that the distal end of the blade 238 is oriented in front of the clip 10c. When the lever 278 of the ratchet 270 engages the second advancer notch 274b, the cutting edge of the blade 238 is positioned in front of the second clip 10c. Further distal motion of the advancer 240 moves both the blade 238 and the pusher bar 256 such that the blade 256 and clip 10c are advanced together. After the clip 10c is deployed from the device, the process can be repeated to deploy the proximal clip 10e. After the proximal clip 10e has been deployed, a lockout mechanism 290 of the pusher bar 256, shown in FIG. 12B, can engage the clip opening mechanism 220 to prevent the pusher bars 256 from being advanced past the distal end of the cartridge assembly 118 and into the opposed jaws 112 of the clip applier 100.

Figure 13A:
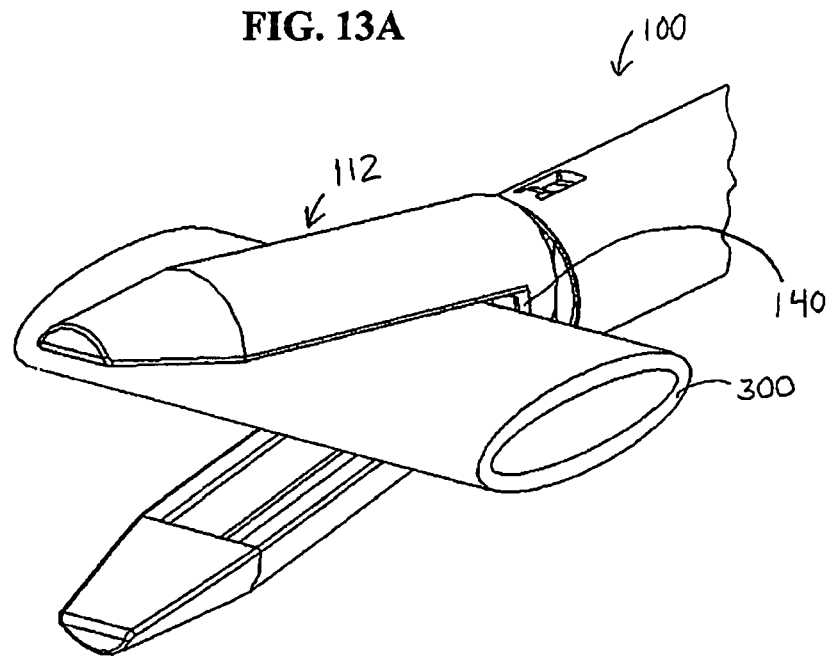
FIG. 13A is a perspective view of the jaws of the clip applier of FIG. 4A disposed around tissue.
Figure 13B:
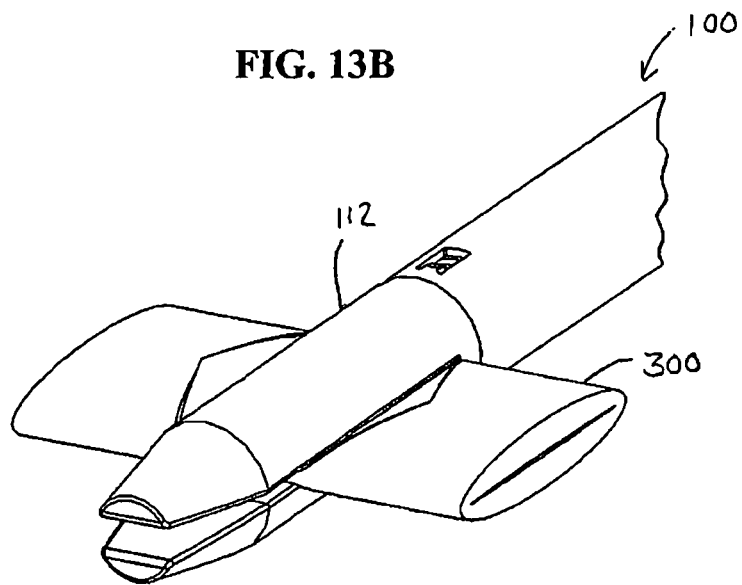
FIG. 13B is a perspective view of the jaws of the clip applier of FIG. 4A in a closed position to engage the tissue.

FIGS. 13A-13D illustrate an embodiment of the clip applier 100 being used to incise and ligate a tissue, such as vessel 300. In FIG. 13A, opposed jaws 112 of the clip applier 100 are disposed in proximity to a vessel 300 to be ligated and moved to an opened position. For example, the elongate shaft of the clip applier 100 can be inserted into the cannula of a trocar implanted within a patient and advanced therein to the location of the vessel 300. The vessel 300 can be disposed between the opened jaws 112 until the vessel reaches the tissue stop 140. In FIG. 13B, the opposed jaws 112 are closed onto the vessel to compress and seal the vessel. Such closure can be effected, for example, by rotating the first moveable handle 106 of the clip applier 100 toward the stationary handle 104 to activate the jaw closing assembly 116 and move the jaws 112 from the open to the closed position.

Figure 13C:
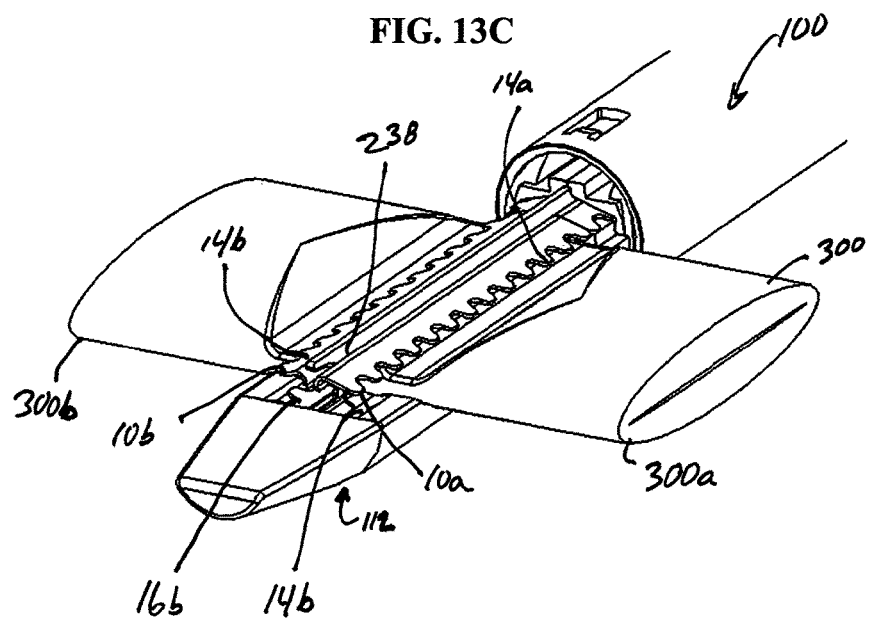
FIG. 13C is a sectional perspective view of the jaws shown in FIG. 13B, with one of the jaws removed to show a cutting element and clips disposed therein.
Figure 13D:
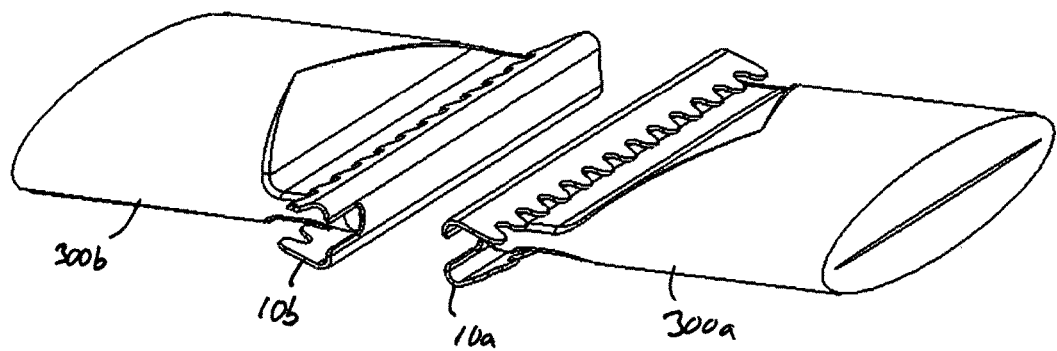
FIG. 13D is a perspective view of the tissue after application of the clips thereto.

In FIG. 13C, the vessel 300 disposed between the jaws 112 is incised and clips are advanced over the incised tissue portions. For example, the second moveable handle 108 of the clip applier 100 can be rotated toward the stationary handle 104 to position the clips from a biased closed position to an open position. Further rotation of the handle 108 causes the cutting element 238 to be advanced into the knife channel 142 of the jaws 112, thereby incising the vessel 300 and forming vessel portions 300a, 300b. The opened clips can then be advanced into the clip guides 137 of the closed jaws 112 behind the cutting element 238 such that the vessel portion 300a is disposed between the arms 14a, 16a of one clip 10a and the vessel portion 300b is disposed between the arms 14b, 16b of another clip 10b. During this procedure, the force required to rotate the second moveable handle 108 to deploy the clips 10a, 10b to the vessel 300 (e.g., the "force to fire") is relatively low and can be in the range of about 3 pounds force to five pounds force. In FIG. 13D, the clips 10a, 10b are released from the clip applier 100 and can return to a biased closed state to ligate the vessel portions 300a, 300b.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical fastener delivery system, comprising:
a delivery device having a handle housing and an elongate shaft extending from the handle housing, the elongate shaft having a lumen extending therethrough from the handle housing to a distal end of the elongate shaft, and the elongate shaft having opposed jaws disposed at the distal end thereof and operable to move between an open, spaced-apart position and a closed position;
a cutting element disposed within the delivery device;
a fastener supply disposed within the delivery device, the fastener supply including a plurality of arcuate fasteners frangibly separable from the fastener supply, the fastener supply being configured to engage tissue on opposite sides of the cutting element, the plurality of fasteners being configured to move from a closed position to an open position, and the plurality of fasteners being biased to the closed position in a resting state; and
a fastener advancing assembly disposed within the delivery device and configured to deploy the plurality of fasteners as the fastener advancing assembly is advanced.

2. The system of claim 1, wherein the plurality of fasteners comprises a first plurality of fasteners positioned on a first side of the cutting element and a second plurality of fasteners positioned on a second side of the cutting element.

3. The system of claim 1, wherein the plurality of fasteners are stored in a first orientation and deployed in a second orientation.

4. The system of claim 1, wherein the fastener advancing assembly is configured to advance distally through the fastener supply.

5. The system of claim 1, wherein advancement of the fastener advancing assembly is configured to cause the plurality of fasteners to sequentially frangibly separate from the fastener supply.

6. The system of claim 1, wherein the plurality of fasteners are configured to move from the open position to the closed position.

7. The system of claim 1, further comprising a pivotable trigger on the delivery device, the pivotable trigger being configured to move the plurality of fasteners to the open position when squeezed.

8. A surgical fastener delivery system, comprising:
a handle;
an elongate shaft extending distally from the handle and having a lumen extending therethrough from the handle to a distal end of the elongate shaft;
an end effector having opposed jaws that are movable between an open position and a closed position;
a cutting element disposed within at least one of the opposed jaws of the end effector and configured to advance through the end effector to cut tissue engaged between the opposed jaws;
a fastener supply disposed within one of the opposed jaws of the end effector, the fastener supply including a first plurality of fasteners disposed on a first side of the cutting element and a second plurality of fasteners disposed on an opposite second side of the cutting element, the first and second plurality of fasteners being frangibly separable from the fastener supply, a length of the first and second plurality of fasteners being configured to be selectively alterable upon separation, the first and second plurality of fasteners being configured to move from a closed position to an open position, and the first and second plurality of fasteners being biased to the closed position in a resting state; and
a fastener deployment member slidably disposed within the end effector and configured to deploy the first and second plurality of fasteners into tissue engaged between the opposed jaws.

9. The system of claim 8, wherein the first and second plurality of fasteners are frangibly separable from the fastener supply at a plurality of discrete locations longitudinally spaced apart from one another along a length of the fastener supply.

10. The system of claim 8, wherein the fastener deployment member is configured to slidably advance between the first and second plurality of fasteners.

11. The system of claim 8, wherein the fastener deployment member is configured to cause the first and second plurality of fasteners to frangibly separate from the fastener supply as the fastener deployment member is advanced through the end effector.

12. The system of claim 8, wherein the first and second plurality of fasteners are stored in a first orientation and deployed in a second orientation.

13. The system of claim 8, wherein the first and second plurality of fasteners are configured to move from the open position to the closed position.

14. The system of claim 8, further comprising a pivotable trigger on the handle, the pivotable trigger being configured to move the first and second plurality of fasteners to the open position when squeezed.

15. A surgical fastener delivery system, comprising:
a delivery device having a handle and an elongate shaft extending from the handle, the handle having a pivotable trigger and a rotation knob configured to rotate the elongate shaft relative to the handle, the elongate shaft having a lumen extending therethrough from the handle to a distal end of the elongate shaft, and the elongate shaft having opposed jaws disposed at the distal end thereof and operable to move between an open, spaced-apart position and a closed position;
a fastener supply disposed within the delivery device and having a plurality of fasteners frangibly separable from the fastener supply, the fastener supply including a cutting element formed on a distal end thereof, and the fastener supply being configured to engage tissue on opposite sides of the cutting element, the plurality of fasteners being configured to move from a closed position to an open position, and the plurality of fasteners being biased to the closed position in a resting state; and
a fastener advancing assembly disposed within the delivery device and configured to deploy the plurality of fasteners as the fastener advancing assembly is advanced.

16. The system of claim 15, wherein the pivotable trigger is configured to move the plurality of fasteners to the open position when squeezed.

17. The system of claim 15, wherein the plurality of fasteners are configured to move from the open position to the closed position.

* * * * *